United States Patent [19]

Builder et al.

[11] Patent Number: 5,723,310
[45] Date of Patent: *Mar. 3, 1998

[54] AQUEOUS MULTIPLE-PHASE ISOLATION OF POLYPEPTIDE

[75] Inventors: Stuart Builder, Belmont; Roger Hart, Burlingame; Philip Lester, San Lorenzo; John Ogez, Redwood City; David Reifsnyder, San Mateo, all of Calif.

[73] Assignee: Genentech, Inc., South San Francisco, Calif.

[ * ] Notice: The term of this patent shall not extend beyond the expiration date of Pat. No. 5,407,810.

[21] Appl. No.: 385,187

[22] Filed: Feb. 7, 1995

Related U.S. Application Data

[63] Continuation of PCT/US94/09089, Aug. 10, 1994, which is a continuation of Ser. No. 110,663, Aug. 20, 1993, Pat. No. 5,407,810.

[51] Int. Cl.$^6$ .............................. C07K 1/20; C07K 14/65; C07K 14/61; C12N 1/00
[52] U.S. Cl. .................. 435/69.1; 530/402; 530/422; 530/399; 435/70.1; 435/803; 435/804
[58] Field of Search ........................ 530/422, 402, 530/399; 435/69.1, 70.1, 803, 804

[56] References Cited

U.S. PATENT DOCUMENTS

| | | | |
|---|---|---|---|
| 4,565,785 | 1/1986 | Gilbert | 435/172.3 |
| 4,579,661 | 4/1986 | Gustafsson et al. | 210/635 |
| 4,673,641 | 6/1987 | George et al. | 530/412 |
| 4,684,723 | 8/1987 | Dove et al. | 530/351 |
| 4,690,892 | 9/1987 | Ananthapadmananhan et al. | 530/422 |
| 4,710,473 | 12/1987 | Morris | 435/172.3 |
| 4,738,921 | 4/1988 | Bellagaje et al. | 935/41 |
| 4,795,706 | 1/1989 | Hsiung et al. | 435/172.3 |
| 4,843,155 | 6/1989 | Chomczynski | 536/25.41 |
| 4,879,234 | 11/1989 | Cordes et al. | 435/921 |
| 4,961,969 | 10/1990 | Hershenson et al. | 435/69.51 |
| 5,093,254 | 3/1992 | Giuliano et al. | 530/422 |
| 5,158,875 | 10/1992 | Miller et al. | 435/69.1 |
| 5,210,028 | 5/1993 | Schmitz et al. | 435/69.4 |
| 5,288,931 | 2/1994 | Chang et al. | 530/399 |
| 5,407,810 | 4/1995 | Building et al. | 435/69.1 |
| 5,410,026 | 4/1995 | Chang et al. | 530/422 |
| 5,459,052 | 10/1995 | Skriver et al. | 435/69.4 |

FOREIGN PATENT DOCUMENTS

| | | |
|---|---|---|
| 23943016 A1 | 5/1981 | Germany . |
| 288837 A5 | 11/1988 | Germany . |
| 298424 A5 | 11/1989 | Germany . |
| WO 88/08003 | 10/1988 | WIPO . |
| WO 91/02089 | 2/1991 | WIPO . |
| WO 92/07868 | 5/1992 | WIPO . |

OTHER PUBLICATIONS

Franks et al., "The Role of Solvent Interactions in Protein Conformation" *CRC Crit. Rev. Biochem.* 3:165–219 (1975).
Kula, "Liquid–Liquid Extraction of Biopolymers" *Comprehensive Biotechnology*, A. Humphrey and C.L. Clooney, New York:Pergamon Press vol. 2:451–471 (1985).
Tanford, "Protein Denaturation—Part C—Theoretical Models for the Mechanism of Denaturation" *Adv. Prot. Chem.* 24:69–72 (1970).
Albertsson, "Aqueous polymer–phase systems" *partition of Cell Particles and Cell Macromolecules* pp. 8–39 (1986).
Albertsson, "Biotechnical applications" *Partition of Cell Particles and Macromolecules* pp. 212–226 (1986).
Albertsson, "Factors determining partition" *Partition of Cell Particles and Cell Macromolecules* pp. 56–111 (1986).
Albertsson, "History of aqueous polymer two–phase partition" *Partitioning in Aqueous Two–Phase Systems*, Walter et al., ed. pp. 1–10 (1985).
Baskir et al., "Thermodynamics of the separation of biomaterials in two–phase aqueous polymer systems: effect of the phase–forming polymers" *Macromolecules* 20:1300–1311 (1987).
Becker et al., "Downstream processing of proteins" *Biotech Advs.* 1:247–261 (1983).
Birkenmeier et al., "Dye–promoted precipitation of serum proteins. Mechanism and application" *Journal of Biotechnology* 21:93–108 (1991).
Birkenmeier et al., "Partition of purified human thyroxine–binding globulin in aqueous two–phase systems in response to reactive dyes" *Journal of Chromatography* pp. 193–201 (1986).
Blomquist et al., "A study of DNA from chloroplasts separated by counter–current distribution" *Acta Chemica Scandinavia* pp. 838–842 (1975).
Blomquist et al., "A study of extraction columns for aqueous polymer two–phase systems" *Journal of Chromatography* pp. 125–133 (1972).
Brems D. et al., "Equilibrium denaturation of pituitary— and recombinant–derived bovine growth hormone" *Biochemistry* 24(26):7662–7668 (1985).
Cole, "Alt–PEG Two–Phase Aqueous Systems to Purify Proteins and Nucleic Acid Mixtures" *Frontiers BioProcess II* pp. 340–351 (1992).
Cole, "Purification of Plasmid and High Molecular Mass DNA Using PEG–Salt Two–Phase Extraction" *BioTechniques* 11(1):18–24 (1991).
Erlanson–Albertsson, "Measurement of the binding of colipase to a triacylglycerol substrate" *Biochemica et Biophysica Acta* 617:371–382 (1980).
Foster et al., "Interactions of human sperm acrosomal protein SP–10 with the acrosomal membranes" *Biology of Reproduction* 46:981–990 (1992).

(List continued on next page.)

*Primary Examiner*—Stephen Walsh
*Assistant Examiner*—David S. Romeo
*Attorney, Agent, or Firm*—Janet E. Hasak

[57] ABSTRACT

A method is described for isolating an exogenous polypeptide in a non-native conformation from cells, such as an aqueous fermentation broth, in which it is prepared comprising contacting the polypeptide with a chaotropic agent and preferably a reducing agent and with phase-forming species to form multiple aqueous phases, with one of the phases being enriched in the polypeptide and depleted in the biomass solids and nucleic acids originating from the cells. Preferably, the method results in two aqueous phases, with the upper phase being enriched in the polypeptide.

26 Claims, 12 Drawing Sheets

OTHER PUBLICATIONS

Glossmann et al., "The preparation of brush border membranes from rat kidney using an aqueous two–phase polymer system" *Naunyn–Schmiedenberg's Arch. Pharmacol.* 282:439–444 (1974).

Grunfield et al., "Effector–assisted refolding of recombinant tissue–plasminogen activator produced in *Escherichia coli*" *Applied Biochemistry and Biotechnology* 33(2):117–138 (1992).

Hattori et al., "Studies of the high molecular weight form of polypeptide chain elongation factor–1 from pig liver" *J. Biochem* 88:725–736 (1980).

Haynes et al., "Electrostatic potentials and protein partitioning in aqueous two–phase systems" *AIChE Journal* pp. 1401–1409 (Sep. 1991).

Hejnaes et al., "Development of an optimized refolding process for recombinant Ala–Glu–IGF–1" *Protein Engineering* 5(8):797–806 (1992).

Hustedt et al., "Applications of phase partitioning in biotechnology" *Patitioning in Aqueous Two–Phase Systems*, Walter et al., ed. pp. 529–587 (1985).

Johansson, "Partitioning of proteins" *Partitioning in Aqueous Two–Phase Systems*, Walter et al., ed. pp. 161–226 (1985).

Johansson et al., "Affinity partitioning of biopolymers and membranes in Ficoll–Dextran aqueous two–phase systems", *Journal of Chromatography* 331:11–21 (1985).

Johansson et al., "Effects of organic solvents on the partitioning of enzymes in aqueous two–phase systems" *Journal of Chromatography* 388(2):295–305 (1987).

Kessel et al., "Effect of dithiocarbanilates on some biological and biophysical properties of leukemia L1210 cell membranes" *Molecular Pharmacology* pp. 1121–1129 (1978).

Kowalczyk et al., "Enzymic synthesis of 1–o (indol–3–ylacetyl)–beta–D–glucose. Purification of the enzyme from *Zea mays*, and preparation of antibodies to the enzyme" *Biochemical Journal* 279(Pt. 2):509–514 (1991).

Kroner et al., "Evaluation of crude dextran as phase–forming polymer for the extraction of enzymes in aqueous two–phase systems in large scale" *Biotechnology & Bioenineering* pp. 1015–1045 (1982).

Ku et al., "Affinity–specific protein separations using ligand–coupled particles in aqueous two–phase systems: I. process concept and enzyme binding studies for pyruvate kinase and alcohol dehydrogenase from *saccharomyces cerevisiae*" *Biotechnology & Bioengineering* 33:1081–1088 (1989).

Kuboi et al., "Kagaku Kogaku Rombun Shu, Kagaku Kogaku Ronbunshu" *KKRBAW* (abstract only, ISSN 0386–216X) pp. 772–779 (1990).

Kuboi et al, "Kagaku Kogaku Rombun Shu, Kagaku Kogaku Ronbunshu" *KKRBAW* (abstract only, ISSN 0386–216X) pp. 1053–1059 (1990).

Kula et al., "Extraction processes" *8th International Biotechnology Symposium* pp. 612–622 (1988).

Kula et al., "Purification of enzymes by liquid–liquid extraction" *Advances in Biochemical Engineering* pp. 73–118 (1982).

Lee et al., "Partitioning of recombinant interleukin–2 is a poly(ethylene–glycol)–dextran aqueous two–phase system" *J. Microbiol. Biotech.* (Chem. Abst. 119:7235, Abstr. #7250r (1993)) 2(2):135–140 (1992).

Lemoine et al., "Active uptake of sucrose by plant plasma membrane vesicles: determination of some important physical and energetical parameters" *Physiologica Plantarum* 82:377–384 (1991).

Lillehoj et al., "Protein purification" *Advances in Biochemical Engineering–Biotechnology* 40:19–71 (1989).

Lundberg S. et al., "Characterization of calcium binding to spectrins" *Biochemistry* 31(24):5665–5671 (Jun. 1992).

Mak. S., et al., "Purification of adenovirus messenger ribonucleic acid by an aqueous polymer two–phase system" *Biochemistry* 15(26):5754–5761 (1976).

Marciani et al., "Polypeptide composition of cell membranes from chick embryo fibroblasts transformed by rous sarcoma virus" *Biochimica et Biophysica Acta* 401 (3):386–398 (Sep. 1975).

Mattiasson et al., "Use of aqueous two–phase sytems for recovery and purification in biotechnology" *Separ Recovery Purif: Math Model* pp. 78–92 (1986).

Mendieta et al., "Affinity–mediated modification of electrical charge on cell surface: a new approach to the affinity partitioning of biological particles" *Analytical Biochemistry* 200(2):280–285 (Feb. 1992).

Moudgil et al., "In vitro modulation of rat liver glucocorticoid receptor by urea" *Journal of Biological Chemistry* 262(11):5180–5187 (Apr. 1987).

Nifant'eva et al., "Extraction of thiocyanate and halide metal complexes in two–phase aqueous systems polyethylene glycol–salt–water" *Journal of Analytical Chemistry of the USSR* 44(8):1105–1110 (1989).

Niwa et al., "Changes in surface hydrophobicity of fish actomyosins induced by urea" *Nippon Suisan Gakkaishi* (bulletin of the Japanese Society of Scientific Fisheries) 55:143–146 (1989).

O'Brien et al., "Merocyanine 540–sensitized photoinactivation of evelpoed viruses in blood products: site and mechanism of phototoxicity" *Blood* 80:277–285 (1992).

Ogez et al., "Downstream processing of proteins: recent advances" *Biotech Adv.* 7:467–488 (1989).

Ohlsson et al., "A rapid method for the isolation of circular DNA using an aqueous two–phase partition system" *Nucleic Acids Research* 5(2):583–590 (1978).

Owusu et al., "Correlation between microbial protein thermostabilty and resistance to denaturation in aqueous: organic solvent two–phase systems" *Enzyme Microb. Technology* 11:568–574 (1989).

Pruul et al., "Hydrophobic characterization of *Helicobacter (Campylobacter) pylori*" *Med. Microbiol.* 12:93–100 (1990).

Raschdorf et al., "Location of disulphide bonds in human insulin like growth factors (IGFs) synthesized by recombinant DNA technology" *Biomedical and Enviromental Mass Spectrometry* 16:3–8 (1968).

Sandstrom et al., "Latency of plasma membrane $H^+$–ATPase in vesicles isolated by aqueous phase partitioning" *Plant Physiol.* pp. 693–698 (1987).

Saskawa et al., "Blood Clam (*Anadara inflata*) Hemoglobins. Partition in Aqueous Two–Polymer Phase Systems and Alkali Denaturation" *Biochimica Biophysica Acta* 244(2):461–465 (1971).

Tanaka et al., "The effect of hydrochloric acid on hydrophobicity and partition of protein in aqueous two–phase sysems" *Journal of Chemical Engineering of Japan* 24(5):661–663 (1991).

Tjerneld et al., "Affinity liquid–liquid extraction of lactate dehydrogenase on a large scale" *Biotechnology Bioengineering* pp. 809–816 (1987).

Wang et al., "Stability and partition of alcohol dehydrogenase in polyethylene glycol/phosphate affinity aqueous two–phase sytems using a triazine dye" *Society of Chemical Engineers, Japan* pp. 134–139 (1992).

Widell et al., "Binding of phytochrome to plasma membranes in vivo" *Physiol. Plant* 61:27–34 (1984).

Zaslavsky et al., "Distribution of inorganic salts between the coexiting phases of aqueous polymer two–phase systems" *Journal of Chromatography* pp. 267–281 (1988).

Zaslavsky et al., "Influence of ionic and polymer composition of the properties of the phases of aqueous two–phase systems formed by non–ionic polymers" *J. Chem. Soc. Faraday Trans.* pp. 141–145 (1991).

Hart et al., "Effect of environment on insulin–like growth factor I refolding selectivity" *Chem. Ab.* (abstract No. 246594d) 121(21):214 (1994).

Sanki Engineering Co., Ltd., "Method for purification of biologically active proteins" *Chem. Ab.* (abstract No. 18765g) 99(3):296 (1983).

FIG. 2

EcoRI (1149)
5'-GAATTCATGAGATTTCCTTCAATTTTACTGCAGTTTTATTCGCAGCATCCTCCGCATTAGC

TGCTCCAGTCAACACTACAACAGAAGATGAAACGGCACAAATTCCGGCTGAAGCTGTCATCGGTT

ACTTAGATTTAGAAGGGGATTTCGATGTTGCTGTTTGCCATTTCCAACAGCACACAAATAACGGG

TTATTGTTTATAAATACTACTATTGCCAGCATTGCTGCTAAAGAAGAAGGGGTATCTTTGGATAA

HaeII                   PstI
AAGAGGTCCGGAAACTCTGTGCGGCGCTGAGCTGGTTGACGCTCTGCAGTTCGTATGTGGTGATC

BamHI
GAGGCTTCTACTTCAACAAACCGACTGGGTACGGATCCTCCTCGTCGTGCTCCGCAAACCGGC

ATCGTTGATGAATGCTGTTTTCGGTCCGTGACCTTCGCGTCTGAAATGTACTGGCTCCGCT

SalI  EcoRI (1633)
GAAACCGGCTAAGTCTGCATAGTCGACGAATTC-3'

AQUEOUS MULTIPLE-PHASE ISOLATION OF POLYPEPTIDE

This application is a continuing application of application PCT/US94/09089 filed 10 Aug. 1994, which is a continuing application of U.S. Ser. No 08/110,663 filed 20 Aug. 1993, now U.S. Pat. No. 5,407,810, all of which applications are incorporated herein by reference.

BACKGROUND OF THE INVENTION

1. Field of the Invention

This application is directed to a method of isolating a polypeptide in non-native form from cells in which it is made. More particularly, the invention relates to a method of isolating a polypeptide in non-native conformation from cells using a multiple-phase aqueous isolation technique.

2. Description of Related and Background Art

The use of recombinant DNA techniques to express DNA encoding heterologous protein has opened new possibilities to produce protein products in commercial quantities. By these methods, the gene encoding the product of interest is introduced into a host cell, e.g., bacteria, fungi, yeast, or mammalian cells, which can be grown in culture so that the gene will become expressed in the cello Polypeptides so produced can be purified and used for a number of applications, including pharmaceutical and veterinarian uses and, in the case of enzymes, food industry or detergent uses.

Producing recombinant protein involves transforming or transfecting host cells with DNA encoding the desired exogenous protein and growing the cells and placing them under conditions favoring production of the recombinant protein. The prokaryote $E.$ $coli$ is favored as host because it can be made to produce recombinant proteins at high titers. Numerous U.S. patents on general bacterial production of recombinant-DNA-encoded proteins exist, including U.S. Pat. No. 4,565,785 on a recombinant DNA molecule comprising a bacterial gene for an extracellular or periplasmic carrier protein and non-bacterial gene; U.S. Pat. No. 4,673,641 on co-production of a foreign polypeptide with an aggregate-forming polypeptide; U.S. Pat No. 4,738,921 on an expression vector with a trp promoter/operator and trp LE fusion with a polypeptide such as IGF-I; U.S. Pat. No. 4,795,706 on expression control sequences to include with a foreign protein; and U.S. Pat. No. 4,710,473 on specific circular DNA plasmids such as those encoding IGF-I.

Under some conditions, certain heterologous proteins expressed in large quantities from bacterial hosts are precipitated within the cells in dense aggregates, recognized as bright spots visible within the enclosure of the cells under a phase-contrast microscope. These aggregates of precipitated proteins are referred to as "refractile bodies," and constitute a significant portion of the total cell protein. Brems et al., $Biochemistry,$ 24: 7662 (1985). On the other hand, the aggregates of protein may not be visible under the phase contrast microscope, and the term "inclusion body" is often used to refer to the aggregates of protein whether visible or not under the phase contrast microscope.

Recovery of the protein from these bodies has presented numerous problems, such as how to separate the protein encased within the cell from the cellular material and proteins harboring it, and how to recover the inclusion body protein in biologically active form. The recovered proteins are often predominantly biologically inactive because they are folded into a three-dimensional conformation different from that of active protein. For example, misfolded IGF-I with different disulfide bond pairs than found in native IGF-I has significantly reduced biological activity. Raschdorf et al., $Biomedical$ $and$ $Environmental$ $Mass$ $Spectroscopy,$ 16: 3–8 (1988). Misfolding occurs either in the cell during fermentation or during the isolation procedure. Methods for refolding the proteins into the correct, biologically active conformation are essential for obtaining functional proteins.

In addition to proper refolding, another challenge faced by biochemists and cell biologists is the development of efficient separation methods, both for soluble substances such as proteins and nucleic acids, and for suspended particles, such as cell organelles and whole cells. Upon fermentation of a prokaryotic broth, for example, many complex particles are generated when the cells are disintegrated. Procedures for separating proteins from these mixtures are complicated, providing particles different in size, form, and chemical composition. Also, the particles may aggregate, dissociate, or generally change their state with time and physical or chemical treatment. There is a great need for mild and efficient fractionation methods, particular for those applications where the level of purity of the product must be very high, e.g., at least 99 percent for pharmaceuticals.

Proteins are typically purified by one or more chromatographic methods such as affinity chromatography, ion exchange chromatography, hydrophobic interaction chromatography, gel filtration chromatography, and reverse-phase high-pressure liquid chromatography. Before a crude extract containing a protein of interest is applied to a chromatography column, the protein extract containing the desired product must be separated from solids such as cells and cell debris. This is because all components applied to the column must be able to pass through the gel matrix. Otherwise, the solid components would clog the gel bed and eventually stop the liquid flow completely. Thus, a purification method must be included in the process scheme to separate the product from solid components and usefully from viscous components, such as cells, cell debris, and nucleic acids, respectively.

The most commonly used methods for this purpose are centrifugal separation or microfiltration or both, depending on the product, host cell type, and localization of the product (extracellular, intracellular, bacterial periplasm, etc.). Since a number of different components are present in a mixture, different methods may be needed utilizing different properties of the particles. For example, centrifugation methods, which separate according to size and density of particles, may be complemented by methods in which other properties, such as surface properties, comprise the separation parameter. One of these methods is distribution in a liquid-liquid two-phase system. In such a method, the phase systems may be obtained by mixing water with different polymers, so that they are compatible with particles and macromolecules from biological material.

Aqueous two-phase partitioning was introduced in 1956–1958 with applications for both cell particles and proteins. Since then, it has been applied to a host of different materials, such as plant and animal cells, microorganisms, virus, chloroplasts, mitochondria, membrane vesicles, proteins, and nucleic acids.

The basis for separation by a two-phase system is selective distribution of substances between the phases. For a soluble substance, distribution occurs mainly between the two bulk phases, and the partitioning is characterized by the partition coefficient, which is defined as the concentration of partitioned substance in the top phase, divided by the concentration of the partitioned substance in the bottom phase. Ideally, the partition coefficient is independent of total concentration and the volume ratio of the phases. It is mainly a function of the properties of the two phases, the partitioned substance, and the temperature.

The two-phase systems may be produced by mixing two phase-incompatible polymer solutions, by mixing a polymer solution and a salt solution, or by mixing a salt solution and a slightly apolar solvent. These types of systems, along with aqueous two-phase partitioning methods for separating macromolecules such as proteins and nucleic acids, cell particles, and intact cells are described, for example, in Albertsson, *Partition of Cell Particles and Macromolecules*, 3rd edition (John Wiley & Sons: New York, 1986); Walter et al., *Partitioning in Aqueous Two-Phase Systems: Theory, Methods, Uses, and Applications to Biotechnology*, (Academic Press: London, 1985); and Kula, "Extraction processes—application to enzyme purification (conference paper)," *8th Int. Biotechnol. Symp.* (pt. 1, 612–622), 1988.

Several low-cost two-phase systems are known that can handle protein separations on a large scale. These systems use polyethylene glycol (PEG) as the upper phase-forming polymer and crude dextran (e.g., Kroner et al., *Biotechnology Bioengineering*, 24: 1015–1045 [1982]), a concentrated salt solution (e.g., Kula et al., *Adv. Biochem. Bioeng.*, 24: 73–118 [1982]), or hydroxypropyl starch (Tjerneld et al., *Biotechnology Bioengineering*, 30: 809–816 [1987]) as the lower phase-forming polymer.

Purification of interferon has been achieved by selective distribution of crude interferon solutions in aqueous PEG-dextran systems or PEG-salt systems using various PEG derivatives. German Patent DE 2,943,016.

Two-phase aqueous polymer systems are extensively discussed in the literature. See, e.g., Baskir et al., *Macromolecules*, 20: 1300–1311 (1987); Birkenmeier et al., *J. Chromatogr.*, 360: 193–201 (1986); Birkenmeier and Kopperschlaeger, *J. Biotechnol.*, 21: 93–108 (1991); Blomquist and Albertsson, *J. Chromatogr.*, 73: 125–133 (1972); Blomquist et al., *Acta Chem. Scand.*, 29: 838–842 (1975); Erlanson-Albertsson, *Biochim. Biophys. Acta*, 617: 371–382 (1980); Foster and Herr, *Biol. Reprod.*, 46: 981–990 (1992); Glossmann and Gips, *Naunyn. Schmiedebergs Arch. Pharmacol.*, 282: 439–444 (1974); Hattori and Iwasaki, *J. Biochem. (Tokyo)*, 88: 725–736 (1980); Haynes et al., *AICHE Journal-American Institute of Chemical Engineers*, 37: 1401–1409 (1991); Johansson et al., *J. Chromatogr.*, 331: 11–21 (1985); Johansson et al., *J. Chromatogr.*, 331: 11–21 (1985); Kessel and McElhinney, *Mol. Pharmacol.*, 14: 1121–1129 (1978); Kowalczyk and Bandurski, *Biochemical Journal*, 279: 509–514 (1991); Ku et al., *Biotechnol. Bioeng.*, 33: 1081–1088 (1989); Kuboi et al., *Kagaku Kogaku Ronbunshu*, 16: 1053–1059 (1990); Kuboi et al., *Kagaku Kogaku Ronbunshu*, 16: 755–762 (1990); Kuboi et al., *Kagaku Kogaku Ronbunshu*, 17: 67–74 (1991); Kuboi et al., *Kagaku Kogaku Ronbunshu*, 16: 772–779 (1990); Lemoine et al., *Physiol. Plant*, 82: 377–384 (1991); Lillehoj and Malik, *Adv. Biochem. Eng. Biotechnol.*, 40: 19–71 (1989); Lundberg et al., *Biochemistry*, 31: 5665–5671 (1992); Marciani and Bader, *Biochim. Biophys. Acta*, 401: 386–398 (1975); Mattiasson and Kaul, "Use of aqueous two-phase systems for recovery and purification in biotechnology" (conference paper), 314, *Separ. Recovery Purif.: Math. Model.*, 78–92 (1986); Mendieta and Johansson, *Anal. Biochem.*, 200: 280–285 (1992); Nifant'eva et al., *Zh. Anal. Khim.*, 44: 1368–1373 (1989); O'Brien et al., *Blood*, 80: 277–285 (1992). Ohlsson et al., *Nucl. Acids Res.*, 5: 583–590 (1978); Owusu and Cowan, *Enzyme Microb. Technol.*, 11: 568–574 (1989); Pruul et al., *J. Med. Microbiol.*, 32: 93–100 (1990); Sandstrom et al., *Plant Physiol. (Bethesda)*, 85: 693–698 (1987); Sasakawa and Walter, *Biochim. Biophys. Acta*, 244: 461–465 (1971); Wang et al., *J. Chem. Engineering of Japan*, 25: 134–139 (1992); Widell and Sundqvist, *Physiol. Plant*, 61: 27–34 (1984); Zaslavskii et al., *J. Chrom.*, 439: 267–281 (1988); Zaslavskii et al., *J. Chem. Soc., Faraday Trans.*, 87: 141–145 (1991); U.S. Pat. No. 4,879,234 issued Nov. 7, 1989 (equivalent to EP 210,532); DD (German) 298,424 published Feb. 20, 1992; WO 92/07868 published May 14, 1992; and U.S. Pat. No. 5,093,254. See also Hejnaes et al., *Protein Engineering*, 5: 797–806 (1992).

An aqueous two-phase extraction/isolation system is described by DD Pat. No. 288,837. In this process for selective enrichment of recombinant proteins, a protein-containing homogenate is suspended in an aqueous two-phase system consisting of PEG and polyvinyl alcohol as phase-incompatible polymers. Phase separation is then performed whereby the protein is concentrated in the top phase while most of the biomass is concentrated in the bottom phase. However, this patent does not address how to partition non-native proteins.

Cole, *Biotechniques*, 11: 18–24 (1991) adds chaotropes and detergents to a two-phase aqueous system to inactivate nucleases that might degrade the DNA being isolated. Cole, *Frontiers Bioprocess II*, 340–351 (1992) and Grunfeld et al., *Appl. Biochem. Biotechnol.*, 33: 117–138 (1992) use a two-phase system for reactivation of t-PA or for purification of t-PA from its reactivation mixture. Johansson and Kopperschlaeger, *J. Chrom.*, 388: 295–305 (1987) mention urea as reducing the affinity partitioning effect for alkaline phosphatase. Mak et al., *Biochemistry*, 15: 5754–5761 (1976) purifies RNA using an aqueous polymer two-phase system. Moudgil et al., *J. Biol. Chem.*, 262: 5180–5187 (1987) uses urea or heat to alter the partition coefficient for a receptor. Niwa et al., *Nippon Suisan Gakkaishi-Bulletin of the Jap. Soc. of Scientific Fisheries*, 55: 143–146 (1989); Tanaka et al., *J. Chem. Eng. Jpn.*, 24: 661–664 (1991); and WO 91/02089 published Feb. 21, 1991 report on extraction of nucleic acids. See also U.S. Pat. No. 4,843,155.

The main benefits of the partitioning technique are the method is efficient, easy to scale up, rapid when used with continuous centrifugal separators, relatively low in cost, and high in water content to maximize biocompatibility. Although considerable savings can be made by their use, there are currently relatively few industrial applications of aqueous two-phase systems to purify proteins.

When a protein is to be isolated from a crude extract by two-phase partitioning, recovery is enhanced by having a maximum distribution of the protein between the phases. A large or small partition coefficient relative to that for the rest of the cell protein provides a means for purifying the product. It is further possible to isolate the product using an extreme phase volume ratio, with a volume reduction as the result, and still retain a high yield. When the partition coefficient is high, as is the case for the intracellular enzyme β-galactosidase, the aqueous two-phase partitioning will provide for a purification and concentration of the products in addition to removing cell particles and nucleic acids in one step. Thus, it is possible to collect a product in a PEG-rich top phase, and at the same time displace cell particles and nucleic acids into the salt-rich bottom phase.

The search for extreme partition coefficients, which provide the possibility for achieving a concentrated product with a high yield, has led to use of a number of second-generation aqueous two-phase systems. One example is affinity partitioning, where PEG is covalently coupled to affinity groups and the resulting conjugate is included as a polymer component to enhance partitioning to the PEG-rich phase. These, and similar approaches, can make the aqueous two-phase extraction/isolation very selective for essentially any product. However, the high cost of the modified PEG, problems in finding a suitable affinity group, and the necessity to recycle the modified PEG for economical reasons, make this concept unattractive for large-scale applications. Another concept has been to fuse the product of interest to a protein that has a large partition coefficients or to a peptide sequence containing tryptophan residues, as described by WO 92/7868.

There is a need in the art for a method for directly isolating recombinant polypeptides from culture in situ in the fermentation tank, without requiring that the protein be renatured and without requiring costly ingredients such as derivatized polymers or fusions of product with a peptide or other affinity agent.

Therefore, it is an object of the present invention to provide a procedure for isolating non-native polypeptides from a broth in which they exist with other species.

It is another object to provide an efficient extraction of recombinant proteins from homogenates of fermentation broth.

It is a specific object to provide a multiple-phase aqueous isolation composition for non-native IGF-I from a tank containing the recombinant protein in the form of inclusion bodies.

These and other objects will be apparent to one of ordinary skill in the art.

SUMMARY OF THE INVENTION

Accordingly, this invention provides, in one aspect; a method for isolating from cells an exogenous polypeptide of interest in a non-native conformation comprising contacting the cells with a chaotropic agent in an amount sufficient to extract the polypeptide from the cells and maintain its solubility and with an effective amount of phase-forming species to form multiple aqueous phases, one of which is enriched in the polypeptide and depleted in biomass solids originating from the cells.

In another aspect, the invention provides a method for recovering from cells a biologically active exogenous polypeptide of interest comprising contacting the cells with a chaotropic agent in an amount sufficient to extract the polypeptide, which is initially in a non-native conformation, from the cells and maintain its solubility and with an effective amount of phase-forming species to form multiple aqueous phases, one of which is enriched in the polypeptide and depleted in biomass solids originating from the cells, recovering the polypeptide by separating the phases, and incubating said recovered polypeptide in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 µM of a copper or manganese salt, wherein an oxygen source is introduced, so that refolding of the polypeptide occurs during the incubation.

In a still further aspects the invention provides a multiple-phase aqueous solution comprising a phase enriched in an exogenous polypeptide of interest in a non-native conformation and depleted in biomass solids from cells in which the polypeptide was produced, wherein the aqueous solution also comprises phase-forming species and a chaotropic agent in an amount sufficient to maintain the solubility of the polypeptide.

In a preferred embodiment, the invention provides a method for isolating an exogenous polypeptide of interest in the form of inclusion bodies from a prokaryotic culture medium in a fermentation vessel comprising adding to the fermentation vessel, which contains about 0.1 to 15 mg/mL of the polypeptide; about 0.5 to 6M of a chaotropic agent and an amount of a reducing agent sufficient to reduce the polypeptide; adding from about 4 to 15% (w/w) of a phase-forming salt and from about 5 to 18% (w/w) of a phase-forming polymer so as to form two aqueous phases, whereby one phase is enriched in the polypeptide and depleted in biomass solids originating from the fermentation broth. Most preferably, the concentration of phase-forming salt is about 4–7% (w/w) and the concentration of phase-forming polymer is about 12–18% (w/w), whereby the upper phase is enriched in the polypeptide and depleted in biomass solids originating from the fermentation broth.

The method herein is particularly amenable to mammalian polypeptides (polypeptides that were originally derived from a mammalian organism) that are in the form of inclusion bodies from prokaryotic cells and need to be refolded after they are isolated from the inclusion bodies. The method results in an increase in purity of the non-native polypeptide before the folding step as compared to using traditional steps of harvesting the cells and centrifuging to obtain the polypeptide. The method merely requires reducing agents chaotrope, and phase-forming species, not specialty chemicals such as derivatized PEG, which would add to the overall cost of the process.

Aqueous multiple-phase extraction following in-situ solubilization provides a means for purifying desired recombinant polypeptide to a level at least comparable to that obtained during centrifugal refractile body isolation. The tendency for nucleic acids to partition in aqueous multiple-phase systems to the solids-containing lower phase aids in their removal. Also recombinant protein can be precipitated from isolated light phase or reextracted to achieve further purification and/or polymer removal.

Additionally, certain chemical agents used to form aqueous multiple-phase systems, such as sodium sulfate and ethanol, are found to be protein-refolding enhancers.

BRIEF DESCRIPTION OF THE DRAWINGS

FIG. 2 depicts the nucleotide sequence of the EcoRI-EcoRI fragment (from positions 1149 to 1633) of p200 containing the MF alpha I prepro and IGF-I gene sequences (SEQ. ID NO. 1).

DESCRIPTION OF THE PREFERRED EMBODIMENTS

A. Definitions

Figure 1:
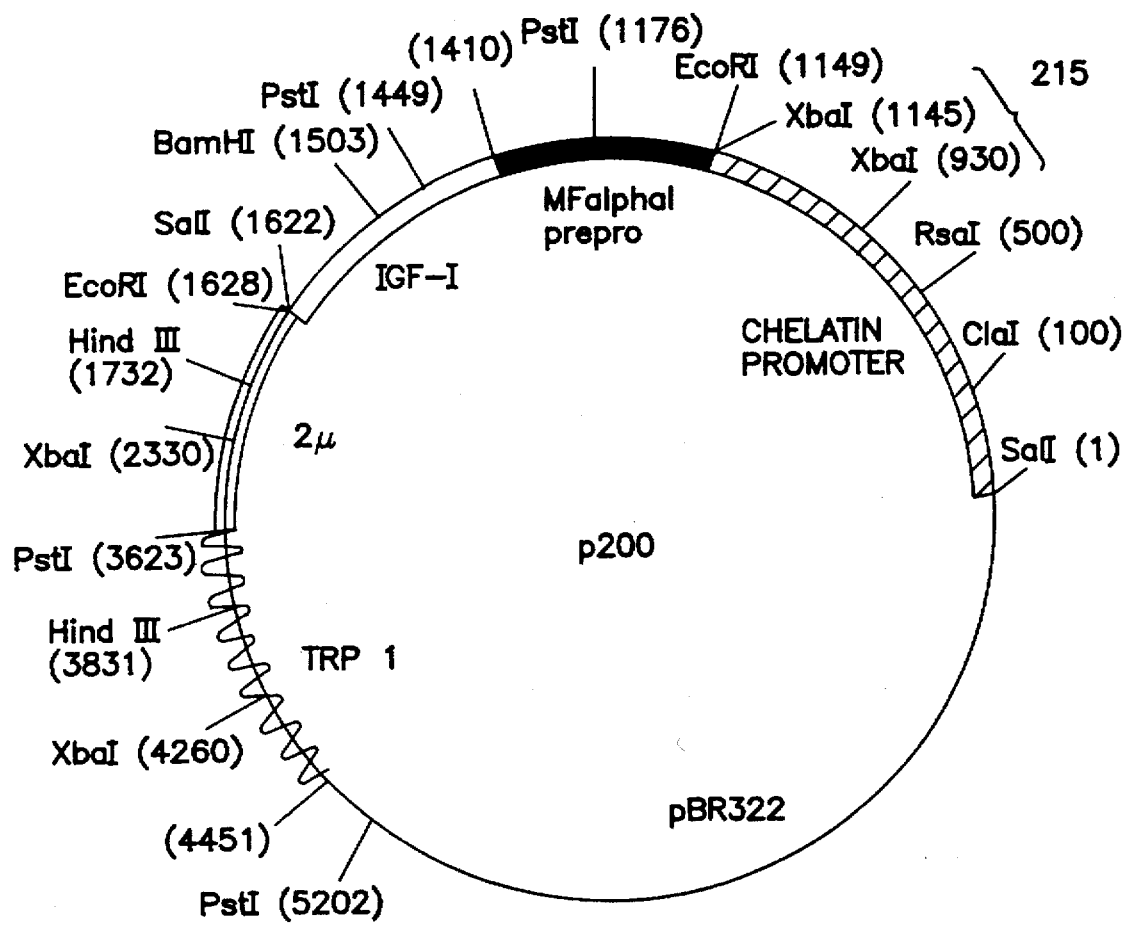
FIG. 1 shows a restriction map for plasmid p200, used to produce pLamBIGF, an intermediate plasmid in the production of pLBIGFTsc, used to prepare pBKIGF-2, an intermediate plasmid in preparing an expression vector encoding IGF-I, namely, pBKIGF-2B.

As used herein, "polypeptide of interest" refers generally to peptides and proteins having more than about ten amino acids. The polypeptides are "exogenous," meaning that they are heterologous, i.e., foreign to the host cell being utilized, such as a human protein produced by a Chinese hamster ovary cell or by a bacterial cell, or a yeast polypeptide produced by a different yeast or a bacterial or mammalian cell. Preferred are mammalian polypeptides produced in prokaryotic cells, most preferably as inclusion bodies in bacterial cells, especially from the periplasm.

Examples of mammalian polypeptides include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; Dnase; inhibin; activin; vascular endothelial growth factor; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

The preferred exogenous polypeptides of interest are those that are easily produced in prokaryotic cells with a minimum of proteolysis and need not be glycosylated for their intended utility. Examples of such mammalian polypeptides include IGF-I, IGF-II, brain IGF-I, growth hormone, relaxin chains, growth hormone releasing factor, insulin chains or pro-insulin, urokinase, immunotoxins, NGF, NT-5, and antigens. Particularly preferred mammalian polypeptides include IGF-I, brain IGF-I, growth hormone, and a neurotrophin such as NGF, NT-3, NT-4, NT-5, and NT-6, including NT-5, and the most preferred mammalian polypeptide is IGF-I.

As used herein, "IGF-I" refers to insulin-like growth factor-I from any species, including bovine, ovine, porcine, equine, and preferably human, in native sequence or in variant form and recombinantly produced. One method for producing IGF-I is described in EP 128,733 published Dec. 19, 1984.

As used herein, the term "inclusion bodies" or "refractile bodies" refers to dense intracellular masses of aggregated polypeptide of interest, which constitute a significant portion of the total cell protein, including all cell components. In some cases, but not all cases, these aggregates of polypeptide may be recognized as bright spots visible within the enclosure of the cells under a phase contrast microscope at magnifications down to 1000 fold.

As used herein, the term "in a non-native conformation" describes polypeptides that assume a secondary, tertiary, and/or quaternary structure that is not the native equivalent. The polypeptide may be in such conformation at any point in the claimed process herein, whether before the contacting step or during or after the contact with chaotropic agent and phase-forming species. The polypeptide in this non-native conformation may be soluble but in an inactive form or may be a non-native membrane proteins or may be insoluble and in a biologically inactive conformation with mismatched or unformed disulfide bonds. This insoluble polypeptide is preferably, but need not be, contained in refractile bodies, i.e., it may or may not be visible under a phase contrast microscope.

As used herein, the term "incorrectly folded" polypeptides refers to precipitated or aggregated polypeptides that are contained within refractile bodies. Non-native polypeptides are obtained from incorrectly folded polypeptides and include correctly folded and misfolded material.

As used herein, the term "cells" refers to any cells; the cells from which the polypeptide of interest is recovered can be treated with the chaotropic agent and phase-forming reagents no matter what their status. For example, the invention encompasses cells in cell culture (whole broth wherein the cells are not separated irrespective of the tank where they are grown) as well as those which have been subjected to homogenization or centrifugation. The phrase "cell culture" refers not only to mammalian cell cultures, but to cultures of any cells, including prokaryotic and yeast cells.

The term "conformers" refers to polypeptides that differ only in intramolecular disulfide bonding. For example, IGF-I is 70 amino acids long and has six cysteine residues that form intramolecular disulfide bonds. The correct, active IGF-I conformer has disulfide bonds between amino acid residues C6-C48, C47-C52, and C18-C61. The other main polypeptide is a biologically less active conformer having disulfide bonds between amino acid residues C6-C47, C48-C52, and C18-C61.

As used herein, the term "fermentation vessel" refers no a tank or other apparatus wherein the culturing of the prokaryotic host takes place so as to produce the polypeptide of interest. The fermentation broth or medium is the culturing medium used for the cells.

As used herein, "chaotropic agent" refers to a compound that, in a suitable concentration in aqueous solution, is capable of changing the spatial configuration or conformation of polypeptides through alterations at the surface thereof so as to render the polypeptide soluble in the aqueous medium. The alterations may occur by changing, e.g., the state of hydration, the solvent environment, or the solvent-surface interaction. The concentration of chaotropic agent will directly affect its strength and effectiveness. A strongly denaturing chaotropic solution contains a chaotropic agent in large concentrations which, in solution, will effectively unfold a polypeptide present in the solution. The unfolding will be relatively extensive, but reversible. A moderately denaturing chaotropic solution contains a chaotropic agent which, in sufficient concentrations in solution, permits partial folding of a polypeptide from whatever contorted conformation the polypeptide has assumed through intermediates soluble in the solution, into the spatial conformation in which it finds itself when operating in its active form under endogenous or homologous physiological conditions. Examples of chaotropic agents include guanidine hydrochloride, urea, and hydroxides such as sodium or potassium hydroxide. Chaotropic agents include a combination of these reagents, such as a mixture of base with urea or guanidine hydrochloride.

As used herein, "reducing agent" refers to a compound that, in a suitable concentration in aqueous solution, maintains sulfhydryl groups so that the intra- or intermolecular disulfide bonds are chemically disrupted. Representative examples of suitable reducing agents include dithiothreitol (DTT), dithioerythritol (DTE), beta-mercaptoethanol (BME), cysteine, cysteamine, thioglycolate, glutathione, and sodium borohydride.

As used herein, "phase-forming species" or "phase-forming reagents" refers to molecules that will act to form multiple phases when added to an aqueous solution. An "aqueous" solution is one wherein the majority of the solution (i.e., greater than about 50%) constitutes water. Thus, for example, 40% ethanol, which contains about 60% water, is a suitable solvent for a phase-forming species. Examples of phase-forming species include polymer-polymer combinations, solvent-salt combinations, polymer-salt combinations, and polymer-solvent combinations. Most preferred herein is the polymer-salt combination.

As used herein, "biomass solids and nucleic acids" refers to particulate (non-dissolved) solids that result (or originate) from the cells or cell culture in which the polypeptide is produced, as well as nucleic acids (DNA, RNA). This would include all sources other than solubilization and liquid extraction component addition. Such solids include, for example, cells, cell debris, media components, cell membranes and vesicles, and proteins endogenous to the cell that are not soluble proteins or other insoluble components of the cell. Upon practicing the method of this invention, the biomass solids and nucleic acids are found in an opposite phase from the polypeptide.

As used herein, the term "multiple" as applied to phases means more than one phase, preferably two to four phases, and most preferably two phases. A phase "enriched in the polypeptide and depleted in biomass solids" refers to a phase wherein the polypeptide has a partition coefficient greater than one and the biomass solids have a partition coefficient less than one, where the partition coefficient is referenced to the phase of interest. For example, if the lower phase is enriched in product, then the partition coefficient is the concentration in the bottom phase divided by the concentration in the top phase.

As used herein, "osmolyte" refers to an agent that lends osmolality to the buffered solution or affects hydration or surface tension. Examples include polyols and sugars such as glycerol, erythritol, arabitol, sorbitol, mannitol, xylitol, mannisidomannitol, glycosyl glycerol, glucose, fructose, sucrose, trehalose, and isofluoroside; polymers such as dextrans, levans, and polyethylene glycol; and some amino acids and derivatives thereof such as glycine, alanine, β-alanine, proline, taurine, betaine, octopine, glutamate, sarcosine, γ-aminobutyric acid, and trimethylamine N-oxide (TMAO), as described more fully in Yancey et al., Science, 217: 1214-1222 (1982) and Schein, Bio/Technology, 8: 308-315 (1990).

As used herein, "buffer" refers to a buffered solution that resists changes in pH by the action of its acid-base conjugate components.

As used herein, "solvent" refers to alcohols and polar aprotic solvents. Alcohols are meant in the sense of the commonly used terminology for alcohol, including alcohols with 1 to 10 carbon atoms, more preferably methanol, ethanol, iso-propanol, n-propanol, or t-butanol, as well as glycerol, propylene glycol, ethylene glycol, polypropylene glycol, and polyethylene glycol, and most preferably ethanol or iso-propanol. Such alcohols are solvents that, when added to aqueous solution, increase the hydrophobicity of the solution by decreasing solution polarity. Polar aprotic solvents are such molecules as dimethyl sulfoxide (DMSO), dimethyl formamide (DMF), N-methylpyrrolidone (NMP), tetrahydrofuran (THF); dioxane, acetonitrile, etc., that can be used in place of or in addition to the alcohol.

As used herein, the phrase "alkaline earth, alkali metals or ammonium salt" refers to a salt having a cation from the alkaline earth or alkali metal elements or an ammonium cation and having an inorganic or organic (hydrocarbon-based) anion. Examples of such salts include sodium chloride, ammonium chloride, sodium citrate, potassium citrate, potassium chloride, magnesium chloride, calcium chloride, sodium phosphate, calcium phosphate, ammonium phosphate, magnesium phosphate, potassium phosphate, sodium sulfate, ammonium sulfate, potassium sulfate, magnesium sulfate, calcium sulfate, etc., Preferred salts herein are chlorides or sulfates. The most preferred salt herein is sodium chloride.

As used herein, the phrasing "copper or manganese salt" refers to a salt of copper or manganese with any anion, including organic anions, that is responsible for promoting oxidation of cysteine residues. Suitable anions include sulfates and chlorides, with copper chloride being particularly preferred. The copper or manganese may be added exogenously or may be residual from the fermentation or otherwise already present in the solution containing the polypeptide of interest.

B. Modes for Carrying Out the invention

This invention relates to a novel means and method for isolating exogenous polypeptides from a complex biological mixture containing polypeptides and non-polypeptides contained in a fermentation broth. It involves contact of reagents with the cells, preferably the cell culture, containing the polypeptide in a non-native conformation, so that an aqueous extraction/isolation can take place. Preferably, the invention entails direct addition of reagents to the fermentation vessel after the polypeptide has been produced recombinantly, thereby avoiding extra steps of harvesting, homogenization, and centrifugation to obtain the polypeptide. While the remaining particulates can be removed by Gaulin homogenization and resuspension, filtration, or a combination thereof, the invention herein utilizes a multiple-phase extraction system for purifying recombinant polypeptides from the remaining particulates.

In particular, this invention is preferred for non-native mammalian polypeptides produced recombinantly in prokaryotic cells, such as bacteria, including *E. coli*, which form refractile bodies in the periplasm of the cells. In this system, one or more denaturants (chaotropic agent), such as urea, guanidine hydrochloride, and/or a base, and a reducing agent, such as dithiothreitol or cysteine, are added to the polypeptide-containing medium and then phase-forming species are added to the broth. Once this second group of reagents is added to the broth, multiple phases are formed whereby one phase is enriched in the polypeptide and depleted in biomass solids and nucleic acids. Preferably, the system has two to four phases, and more preferably two phases, one being enriched in polypeptide and the other being enriched in biomass solids and nucleic acids. Preferably, the desired polypeptide partitions to the upper phase so that the upper phase is enriched in the polypeptide and depleted in the biomass solids and nucleic acids.

Suitable host cells for expressing the DNA encoding the desired polypeptide are the prokaryote, yeast, or higher eukaryote cells. Suitable prokaryotes for this purpose include bacteria such as archaebacteria and eubacteria. Preferred bacteria are eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella; Bacilli such as *B. subtilis* and *B. licheniformis* (e.g., *B. licheniformis* 41P disclosed in DD 266,710 published Apr. 12, 1989); Pseudomonas such as *P. aeruginosa*; Streptomyces; Azotobacter; Rhizobia; Vitreoscilla; and Paracoccus. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting.

Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYA177, or pKN410 are used to supply the replicon.

*E. coli* strain W3110 is a preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 27C7. The complete genotype of 27C7 is tonAΔ ptr3 phoAΔE15 Δ(argF-lac)169 ompTΔ degP41kan$^r$. Strain 27C7 was deposited on Oct. 30, 1991 in the American Type Culture Collection as ATCC No. 55,244. Alternatively, the strain of *E. coli* having mutant periplasmic protease disclosed in U.S. Pat. No. 4,946,783 issued Aug. 7, 1990 may be employed. Alternatively, in vitro methods of cloning, e.g., PCR or other nucleic acid polymerase reactions, are suitable. For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonAΔ ptr3 phoAΔE15 Δ(argF-lac)169 ompTΔ degP41kan$^r$; *E. coli* W3110 strain 37D6, which has the complete genotype tonAΔ ptr3 phoAΔE15 Δ(argF-lac)169 ompTΔ degP41kan$^r$ rbs7Δ ilvG; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

In addition to prokaryotes, eukaryotic microbes such as filamentous fungi or yeast are suitable cloning or expression hosts for polypeptide-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985]; Kluyveromyces hosts (U.S. Pat. No. 4,943,529; Fleer et al., supra) such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., supra), *K. thermotolerans*, and *K. marxianus*; yarrowia [EP 402,226]; *Pichia pastoris* [EP 183,070; Sreekrishna et al., *J. Basic Microbiol.*, 28: 265–278 (1988)]; Candida; Trichoderma reesia [EP 244,234]; *Neurospora crassa* [Case et al., *Proc. Natl. Acad. Sci. USA*, 76: 5259–5263 (1979)]; Schwanniomyces such as *Schwanniomyces occidentalis* [EP 394,538 published Oct. 31, 1990]; and filamentous fungi such as, e.g., Neurospora, Penicillium, Tolypocladium [WO 91/00357 published Jan. 10, 1991], and Aspergillus hosts such as *A. nidulans* [Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

Host cells appropriate for the expression of the DNA encoding the desired polypeptide may also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera fru-*

*giperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47–55 (1988); Miller et al., in *Genetic Engineering*, Setlow, J. K. et al., eds., Vol. 8 (Plenum Publishing, 1986), pp. 277–279; and Maeda et al., *Nature*, 315: 592–594 (1985). A variety of viral strains for transfection are publicly available; e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the DNA encoding the desired polypeptide. During incubation of the plant cell culture with *A. tumefaciens*, the DNA encoding the desired polypeptide is transferred to the plant cell host such that it is transfected, and will, under appropriate conditions, express the DNA encoding the desired polypeptide. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. USA*, 77: 4216 [1980]); mouse sertoli cells (TM4, Mather, *Biol. Reprod.*, 23: 243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* (1990) Vol. 185, pp. 527–537, and Mansour et al., *Nature*, 336: 348–352 (1988).

If prokaryotic cells are used to produce the polypeptide of interest in accordance with the method of this invention, they are cultured in suitable media in which the promoter can be constitutively or artificially induced as described generally, e.g., in Sambrook et al., *Molecular Cloning: A Laboratory Manual* (Cold Spring Harbor Laboratory Press, NY 1989). Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism.

If mammalian host cells are used to produce the polypeptide of this invention, they may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or U.S. Pat. No. 4,560,655; WO 90/03430; WO 87/00195; U.S. Pat. No. Re. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: A Practical Approach*, M. Butler, ed. (IRL Press at Oxford University Press, Oxford, 1991).

The above process can be employed whether the polypeptide is intracellular or in the periplasmic space. The preferred conditions given herein for isolating a polypeptide are directed particularly to inclusion bodies located in the periplasmic space.

After fermentation is complete, the cell culture is contacted with one or more chaotropic agents, an optional reducing agent; and phase-forming reagents so that multiple phases are formed, one phase of which is enriched in the polypeptide of interest. It is preferred to add the chaotrope and reducing agent first to extract the polypeptide from the cell and maintain its solubility in the broth before the phase-forming reagents are added. Also, while the polypeptide of interest can be extracted from (and enriched in) any phase, preferably it is recovered from the uppermost phase.

Most preferably, the chaotropic agent and optional reducing agent are added directly to the fermentation broth in the fermentation vessel before isolation of the polypeptide so that the reagents permeate the cells and the polypeptide is solubilized and diffuses to the surrounding medium. The reducing agent is added if the polypeptide contains at least one sulfhydryl group.

Examples of suitable reducing agents include dithiothreitol (DTT), β-mercaptoethanol (BME); cysteine, thioglycolate, and sodium borohydride. The amount of reducing agent to be present in the buffer will depend mainly on the type of reducing agent and chaotropic agent, the type and pH of the buffer employed, and the type and concentration of the polypeptide in the buffer. An effective amount of reducing agent is that which is sufficient to eliminate intermolecular disulfide-mediated aggregation. For example, with 0.5–6 mg/mL IGF-I in a buffered solution at pH 7.5–10.5 containing 1–4M urea, the DTT concentration is at about 1–20 mM, and the concentration of cysteine is at about 10–50 mM. The preferred reducing agent is DTT at about 2–10 mM or cysteine at about 30–50 mM.

Chaotropic agents suitable for practicing this invention include, e.g., urea and salts of guanidine or thiocyanate, more preferably urea, guanidine hydrochloride, or sodium thiocyanate. The amount of chaotropic agent necessary to be present in the buffer depends, for example, on the type of chaotropic agent and polypeptide present. The amount of chaotropic agent to be added to the fermentation broth will be sufficiently high to extract the polypeptide from the cell and maintain its solubility in the broth. If the polypeptide is to be extracted from the top phased the amount of chaotropic agent must be sufficiently low so that after addition of the phase-forming species; the density is not increased to a point where the solids rise to the top instead of settling to the bottom. Generally the concentration of chaotropic agent is about 0.1 to 9M, preferably about 0.5–9M, more preferably about 0.5 to 6M, and most preferably about 0.5–3M. Also, preferably the chaotropic agent is added to the culture medium before the phase-forming reagents are added. The preferred chaotropic agent herein is urea at about 1.5–2.5M, more preferably at about 2M, or guanidine hydrochloride at about 0.5–3M. Most preferably, the chaotropic agent is urea.

The concentration of the polypeptide in the aqueous solution to which the chaotrope and reducing agent are added must be such that the polypeptide will be recovered in the maximum yield. The exact amount to employ will depend, e.g., on the type of polypeptide and the concentrations and types of other ingredients in the aqueous solution, particularly the reducing agent, chaotropic agent, phase-forming species, and pH. For polypeptides in general, the preferred concentration of polypeptide is about 0.1 to 15 mg/mL. The preferred concentration of IGF-I (resulting in the maximum yield of denatured or non-native IGF-I) is in the range of 0.5–6 mg per mL, more preferably 1.5–5 mg/mL.

The types of phase-forming species to employ herein depend on many factors, including the type of polypeptide and the ingredients in the fermentation broth being treated. The species must be selected so that the polypeptide does not precipitate and one phase is more hydrophobic than the other phase so that the polypeptide will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt, and polymer-solvent combinations. Suitable polymers are both highly hydrophilic polymers and less hydrophilic polymers, i.e., any phase-forming polymers that are known in the art. Examples include polyethylene glycol or derivatives thereof, including various molecular weights of PEG such as PEG 4000, PEG 6000, and PEG 8000, derivatives of PEG described, for example, in Grunfeld et al., supra, polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and Ficoll-400™ polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Such solvents are such that, when added to aqueous solution, they increase the hydrophobicity of the solution.

The salts can be inorganic or organic and preferably do not act to precipitate the polypeptide. Salts containing transition elements are not preferred as they tend to precipitate the polypeptide. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Types of salts that are useful in forming bi-phasic aqueous systems are evaluated more fully in Zaslavskii et al., *J. Chrom.*, supra. Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the polypeptide of interest to obtain a satisfactory multiple-phase system are those known in the art. The amount of phase-forming species added to the polypeptide will depend on such factors as, for example, the amount of chaotropic agent and reducing agent, if any, already present in the fermentation broth, the nature of the cell culture media, the type of cells used in the fermentation, the type of polypeptide being treated, whether the polypeptide will be recovered from the lower or upper phased and the type(s) of phase-forming species being added. The general concentration of polymer employed is about 5% (w/w) up to the limit of solubility for the polymer and the concentration of salt employed is about 3% (w/w) up to the limit of solubility for the salt, depending on the size of the phase-volume ratio needed. The phase-volume ratio must be sufficient to accommodate the biomass solids. The types and amounts of phase-forming species that are effective can be determined by phase diagrams and by evaluating the final result, i.e., the degree of purity and the yield of the polypeptide of interest. If the phase-forming species are a polymer-salt combination, preferably the concentration of salt added is about 4–15% (w/w) and the concentration of polymer is 5–18% (w/w) so that the desired polypeptide will be in an opposite phase from that in which the biomass solids and nucleic acids are present.

If the system desired is one where the polypeptide is distributed in the top phase and the biomass solids and nucleic acids are in the bottom phase, then there is a window of concentrations of phase-forming species. When higher amounts of chaotropic agent are added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized polypeptide, but low enough to allow the biomass solids to sediment to the opposite (lower) phase, If the polypeptide is to be recovered in the upper phase, typically the salt concentration will be about 4–7% (w/w) and the polymer concentration will be about 12–18% (w/w), depending, e.g., on the type of salt, polymer, and polypeptide. If an organic solvent is added as a phase-forming species, such as ethanol, it is preferably added in a concentration of about 10 to 30% (volume/volume) of the solution, depending, e.g., on the type of polypeptide and alcohol and if any other phase-forming species is present, preferably at a concentration of about 20% (v/v).

The exact conditions for contacting the cell culture with the various reagents will depend on, e.g., the pH of the buffer; the types of phase-forming reagents, and the types and concentrations of polypeptide and chaotropic and reducing agents. The reaction temperature is generally about 20°–40° C., more preferably room temperature. The contacting step will generally be carried out for at least about 30 minutes, preferably about 30 minutes to 12 hours depending on whether side-reactions will occur, more preferably about 30 minutes to 8 hours, and most preferably about 30 minutes to 1.5 hours.

If the polypeptide is being unfolded, the degree of unfolding is suitably determined by chromatography of the non-native polypeptide, including hydrophobic interaction chromatography or ion-exchange chromatography. Increasing peak area for the non-native material indicates how much non-native polypeptide is present.

Once the multiple-phase system is established, one phase will be enriched in the polypeptide and depleted in the disrupted particles and cells comprising the biomass solids and nucleic acids. In a two-phase system, preferably the top phase is enriched in the polypeptide whereas the bottom phase is enriched in the disrupted particles and cells. The polypeptide can be easily recovered by separation of the phases. This recovery step may be accomplished by decanting the upper phase, by draining the lower phase, or by centrifugation. The polypeptide can then be isolated from the phase in which it is contained by changing the pH of the phase so as to precipitate the polypeptide or by adding a suitable solvent, whereupon the precipitated polypeptide is suitably recovered by centrifugation or filtration or as a slurry. Alternatively, the polypeptide can be recovered from the polymer-containing phase by re-extraction by addition of a suitable polymers salt, or solvent. In the case of IGF-I, the polypeptide is recovered from the isolated polymer phase by lowering the pH so that the IGF-I will precipitate, resulting in a yield of IGF-I of as much as or more than about 97%.

Once obtained from the liquid phase of the multiple-phase system, or at a later stage of purification, the polypeptide is suitably refolded into an active conformation. One suitable refolding method that can be utilized is that which follows.

After the polypeptide is solubilized and extracted by the multiple-phase extraction system herein, it is placed or diluted into a buffer containing solvent, chaotropic agent, salt, and a minimal amount of a copper or manganese salt. This buffer unexpectedly increases refolding yields of polypeptide from any type of host. This buffer is at a pH of about 7 to 12, depending mainly on the type of polypeptide and reducing agent, preferably about 8 to 11, more preferably pH 8.5 to 11, and most preferably 8.5 to 10.5.

One key ingredient of the buffer is an alcoholic or polar aprotic solvent at a concentration of about 5–40% (v/v), preferably 10 to 30% (volume/volume) of the solution, depending, e.g., on the type of polypeptide and solvent, and the concentration of chaotropic agent. It is most preferably at a concentration of about 20% (v/v).

A second key ingredient to this buffer is an alkaline earth, alkali metal, or ammonium salt, which is present in a concentration of about 0.2 to 3M, preferably 0.2 to 2M, depending mainly on the chaotrope concentration, solvent concentration, and the type of alkaline earth, alkali metal, or ammonium salt and polypeptide employed. For example, if the cation is sodium, potassium, or ammonium, the concentration is about 0.5 to 3M, but if the cation is magnesium, the concentration is about 0.2 to 1M.

A third key ingredient of the buffer is an effective amount of a chaotropic agent. The amount of such chaotrope will depend mainly on the concentration of alkaline earth, alkali metal, or ammonium salt, the concentration of solvent, the specific type of alkaline earth, alkali metal, or ammonium salt employed, the specific type of chaotropic agent employed; and the type of polypeptide, as well as the pH of the buffer, but in general will range from about 0.1 to 9M, preferably about 0.5 to 6M, and most preferably about 1.5 to 4M. As to specific chaotropes, preferably about 0.1 to 2M of guanidine hydrochloride, and preferably about 1–3M, more preferably about 1–2.5M, and most preferably about 2M, of urea is utilized.

A fourth key ingredient of the buffer is an effective amount of a transition metal salt selected from copper and manganese salts so that oxidation and resultant refolding will occur. The amount of copper or manganese salt depends mainly on the type of transition metal and polypeptide employed and the oxygen level present. The lower the rate of oxygen addition or the oxygen level, the higher the amount of copper or manganese salt that can be employed. The copper or manganese salt concentration is typically about 0.01 to 15 μM, preferably about 0.01 to 10 μM, more preferably about 0.01 to 5 μM, and even more preferably about 0.01 to 0.5 µM. The above preferred ranges are particularly preferred for IGF-I. If the concentration is increased beyond about 15 µM, unexpectedly the yield of correctly folded polypeptide decreases dramatically. Most preferably, the concentration of a copper or manganese salt is about 0.5 µM. The transition metal salt may already be present in the buffer without addition of exogenous transition metal salt, for example, if it is residual from the fermentation, or it may be added to the buffer, or both.

The buffer can be any of those listed above for the first buffered solution, with CAPSO, glycine, and CAPS being preferred at pH 8.5–11, particularly at a concentration of about 20 mM, and most preferably CAPSO and glycine. The polypeptide may be diluted with the refolding buffer, preferably at least five fold, more preferably at least about ten fold. Alternatively, the polypeptide may be dialyzed against the refolding buffer. The refolding is typically carried out at about 0°–45° C., preferably about 20°–40° C., more preferably about 23°–37° C., even more preferably about 25°–37° C., and most preferably about 25° C. for at least about one hour. The preferred temperature is not apparently affected by salt, solvent, and chaotropic agent levels; but may be affected by the presence of sucrose and glycerol, in which case it should be kept above about 20° C. The solution optionally also contains a reducing agent and an osmolyte.

The reducing agent is suitably selected from those described above for the solubilizing step in the concentration range given. Its concentration will depend especially on the concentrations of alkaline earth, alkali metal, or ammonium salt, polypeptide, and solvent. Preferably, the concentration of reducing agent is about 0.5 to 8 mM, more preferably about 1–5 mM, even more preferably about 0.5–2 mM. The preferred reducing agents are DTT and cysteine.

The optional osmolyte is preferably sucrose (in a concentration of about 0.25–1M) or glycerol (in a concentration of about 1–4M). More preferably, the sucrose concentration is at about 1M and the glycerol concentration is at about 4M.

The initial concentration of polypeptide in the folding buffer is such that the ratio of correctly folded to misfolded conformer recovered will be maximized, as determined by HPLC, RIA, or bioassay. The exact concentration will depend, for example, on the type of polypeptide employed. The preferred concentration of polypeptide (resulting in the maximum yield of correctly folded conformer) is in the range of about 0.1 to 15 mg/mL, more preferably about 0.1 to 6 mg/mL, and most preferably about 0.2 to 5 mg/mL.

In addition, a source of oxygen such as air or oxygen gas is entrained in or otherwise introduced into the buffer so as to effect oxidation together with the copper or manganese salt. The oxygen can be present in the buffer at any point in timed including before the polypeptide or any other reagents are added to the buffer.

The amount of oxygen source introduced will depend, e.g., on the type of vessel utilized, the type and concentration of polypeptide, the type of oxygen source, the type and amount of copper or manganese salt, and the type and amount of reducing agent present, if any, and the type and amount of chaotropic agent present as well as the pH of the buffer. Generally, the oxygen source will be introduced by passive means (e.g., as air in head space in a ratio of air space to fluid volume of 2:1) using an agitator. Alternatively, the oxygen source may be introduced by bubbling through a sparger. The rate of introduction of the oxygen must be sufficient to allow folding to reach completion in preferably about 1 to 12 hours, more preferably about 1 to 6 hours, and most preferably about 1 to 3 hours. The addition of molar oxygen is proportional to the reductant concentration and polypeptide concentration, but inversely proportional to the copper or magnesium salt concentration. The rate of oxidation is limited by the level of catalyst, not by the oxygen addition rate. A higher sparging rate is required for larger volume folding.

The degree of refolding that occurs upon this second incubation is suitably determined by the RIA titer of the polypeptide or by HPLC analysis using e.g., a Vydac or Baker C-18 column, with increasing RIA titer or correctly folded polypeptide peak size directly correlating with increasing amounts of correct, biologically active polypeptide conformer present in the buffer. The incubation is carried out to maximize the yield of correctly folded polypeptide conformer and the ratio of correctly folded polypeptide conformer to misfolded polypeptide conformer recovered, as determined by RIA or HPLC, and to minimize the yield of multimeric, associated polypeptide as determined by mass balance.

After the polypeptide is refolded, the following procedures are exemplary of suitable purification procedures for obtaining greater purity: fractionation on immunoaffinity or ion-exchange columns; ethanol precipitation; reverse phase HPLC; hydrophobic interaction chromatography; chromatography on silica or on an ion-exchange resin such as S-Sepharose and DEAE; chromatofocusing; SDS-PAGE; ammonium sulfate precipitation; and gel filtration using, for example, Sephadex G-75.

The invention will be more fully understood by reference to the following examples, which are intended to illustrate the invention but not to limit its scope. All literature and patent citations are expressly incorporated by reference.

EXAMPLE I

A. Construction of host cell strain 37D6

The host used to produce recombinant human IGF-I in the fermentation described in this example was a derivative of E. coli W3110, designated 37D6. The complete genotype of 37D6 is tonAΔ ptr3 phoAΔE15 Δrbs7 ilvG Δ(argF-lac)169 ompTΔ degP41kan$^r$. The derivation of strain 27C7, which is a parent strain for 37D6 having the genotype tonAΔ ptr3 phoAΔE15 Δ(argF-lac)169 ompTΔ degP41kan$^r$, is set forth in WO 93/11240 published Jun. 10, 1993, the disclosure of which is incorporated herein by reference. Strain 27C7 was deposited on Oct. 30, 1991 in the American Type Culture Collection as ATCC No. 55,244.

Strain 37D6 is the same as 27C7 described above except for having a rbs7 deletion (ribose utilization minus) and having a restored ilvG locus. Both markers can be introduced by P1 transduction.

B. Description/Construction of IGF-I Expression Plasmid pBKIGF2B

In the IGF-I-expressing plasmid pBKIGF-2B, the transcriptional and translational sequences required for expression of the IGF-I gene in E. coli are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively by the STII signal sequence. The majority of rhIGF-I is found in the cell periplasmic space. Plasmid pBKIGF-2B confers tetracycline resistance upon the transformed host.

Plasmid pBKIGF-2B was constructed in several steps using as intermediate plasmids pLS32Tsc, pLBIGFTsc, pLS33Tsc, and pRanTsc.

Step 1: pLS32Tsc

The secretion plasmid pLS32Tsc contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively the STII signal sequence. The majority of rhIGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS32lamB, pLS33lamB, and pLS33Tsc as disclosed in detail in WO 93/11240, supra.

Step 2: pLBIGFTsc

Step a: pLamBIGF

For the first part of the ligation, the EcoRI-PstI vector fragment from pBR322 was isolated. For the second part of the ligation, a PstI-NcoI 1244-bp fragment was isolated from pAPLamB. For the third part of the ligation, the HaeII-EcoRI 196-bp fragment containing the IGF-I gene except the initial 5' end was isolated from plasmid p200. p200 is a pBR322-derived plasmid having, in the 5' to 3' order, the chelatin promoter; the MF alpha I prepro signal sequence, DNA encoding mature IGF-I, and the 2-micron terminator. It contains the ColE1 origin of replication for bacteria and the 2-micron origin for yeast. A restriction enzyme plasmid diagram of p200 is provided in FIG. 1. The nucleotide sequence (SEQ. ID NO. 1) of the EcoRI (starting at position 1149) to EcoRI (starting at position 1628) fragment of p200 containing the MF alpha I prepro and IGF-I gene is provided in FIG. 2. The HaeII, PstI, BamHI, and SalI restriction sites that are also in the diagram in FIG. 2 are indicated in the sequence by underlining. A piece of synthetic DNA linking the signal sequence to the IGF-I gene (NcoI to HaeII) was prepared having the following sequence:

5'-CATG GCC GGT CCG GAA ACT CTG TGC GGC GC    (SEQ. ID NO. 2)
3'-        CGG CCA GGC CTT TGA GAC ACG C       (SEQ. ID NO. 3).

Figure 3:
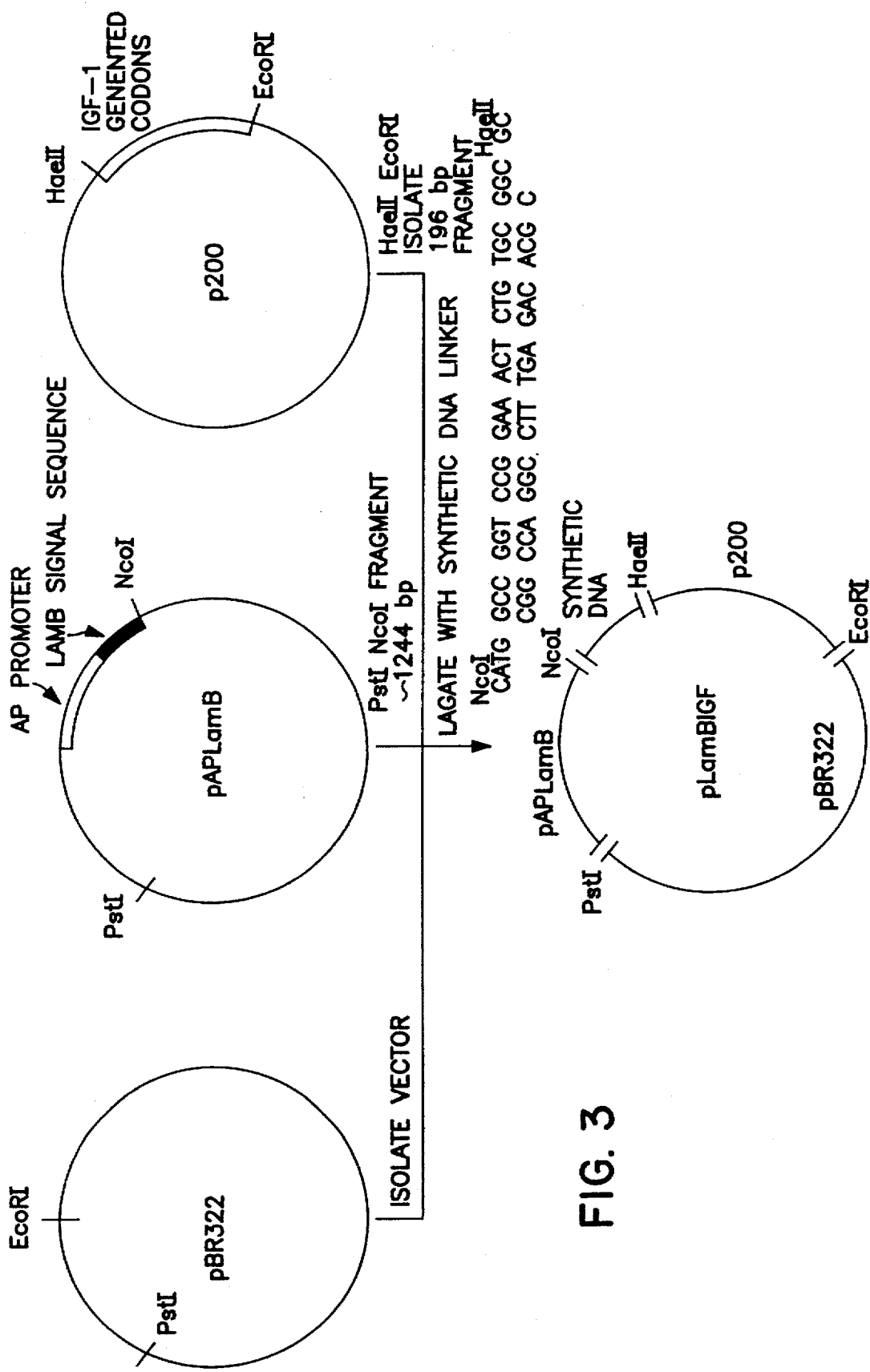
FIG. 3 depicts the construction of pLamBIGF from three plasmid fragments and a piece of synthetic DNA (SEQ. ID NOS. 2 and 3). pLamBIGF is an intermediate plasmid in the production of pLBIGFTsc, used to prepare pBKIGF-2.

The three plasmid fragments and the synthetic DNA were ligated together to form pLamBIGF, as shown in FIG. 3.

5'-CATGGCC GGT CCC GAA ACT CTG TGC GGT GCT GAA CTG GTT GAC GCT CTG CA-3'
3'-         CGG CCA GGG CTT TGA GAC ACG CCA CGA CTT GAC CAA CTG CGA G-5'
(SEQ. ID NOS. 4 and 5, respectively).

Step b: pLBIGFTsc

Figure 4:
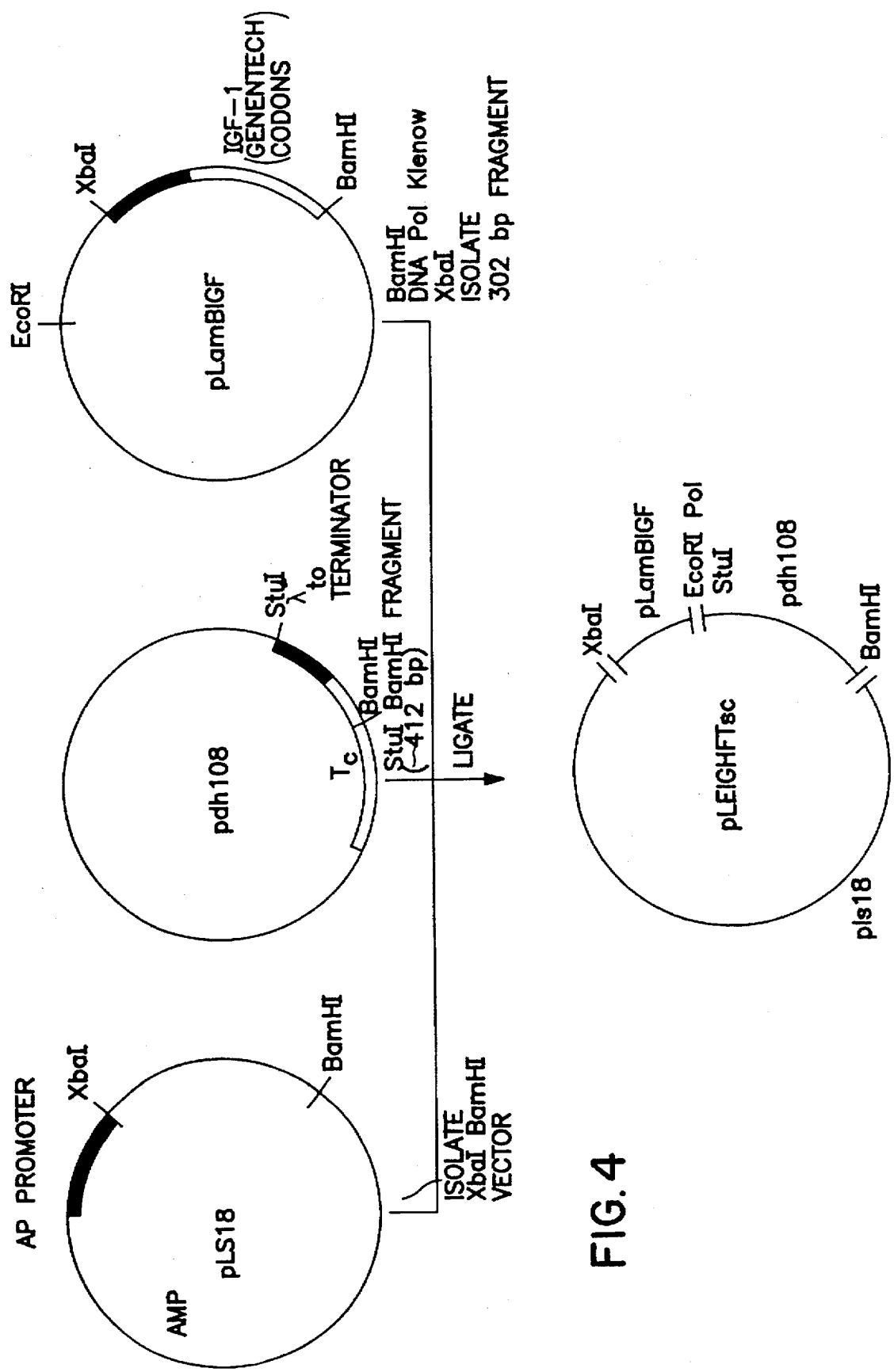
FIG. 4 depicts the construction of the intermediate plasmid pLBIGFTsc from pLamBIGF.

The XbaI-BamHI vector fragment was isolated from pLS18 as the first ligation fragment. The second part of the ligation was a 412-bp StuI-BamHI fragment from the plasmid pdH108-4 described above. The third part of the ligation was prepared by an EcoRI digest of pLamBIGF, followed by treatment with DNA polymerase Klenow fragment, followed by a XbaI digest. The resultant 302-bp fragment was isolated. These three fragments were ligated to yield pLBIGFTsc, as shown in FIG. 4.

Step 3: pRanTsc

Figure 5:
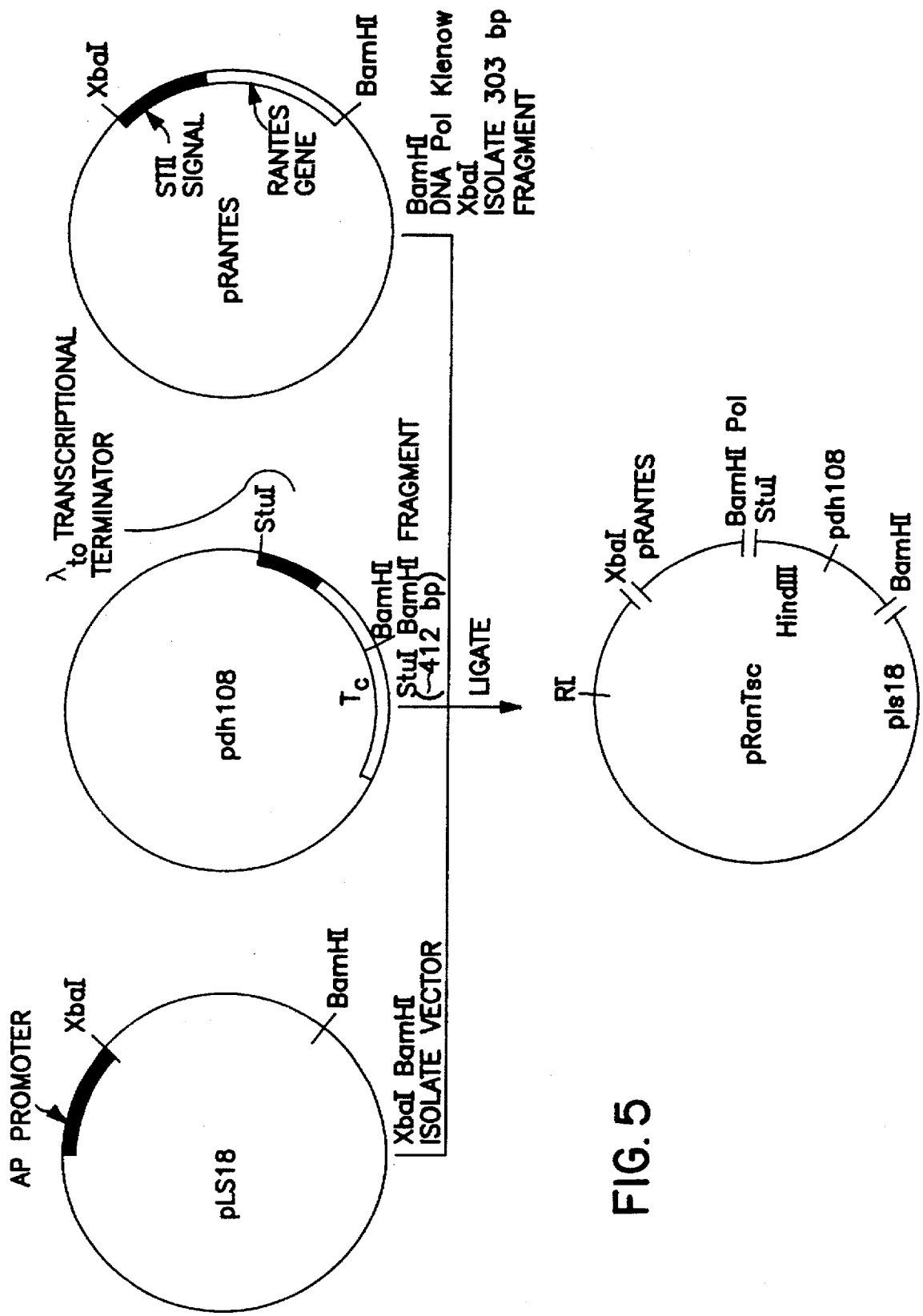
FIG. 5 depicts the construction of the intermediate plasmid pRanTsc used in the production of pBKIGF-2.

The XbaI-BamHI vector fragment from pLS18 was isolated as the first ligation fragment. The second part of the ligation was a 412-bp StuI-BamHI fragment from the plasmid pdH108-4 described above. The third part of the ligation was prepared from pRANTES. pRANTES is a pBR322-based plasmid containing a fragment of a XbaI linker followed by the STII signal, followed by the cDNA encoding RANTES [as published by Schall et al., *J. Immunol.,* 141: 1018 (1988)], followed by the BamHI linker. The third fragment was prepared by digestion of pRANTES with BamHI, followed by treatment with DNA polymerase Klenow fragment, followed by a XbaI digest. The resultant 303-bp fragment was isolated. These three fragments were ligated to yield pRanTsc, as shown in FIG. 5.

Step 4: pBKIGF-2

Figure 6:
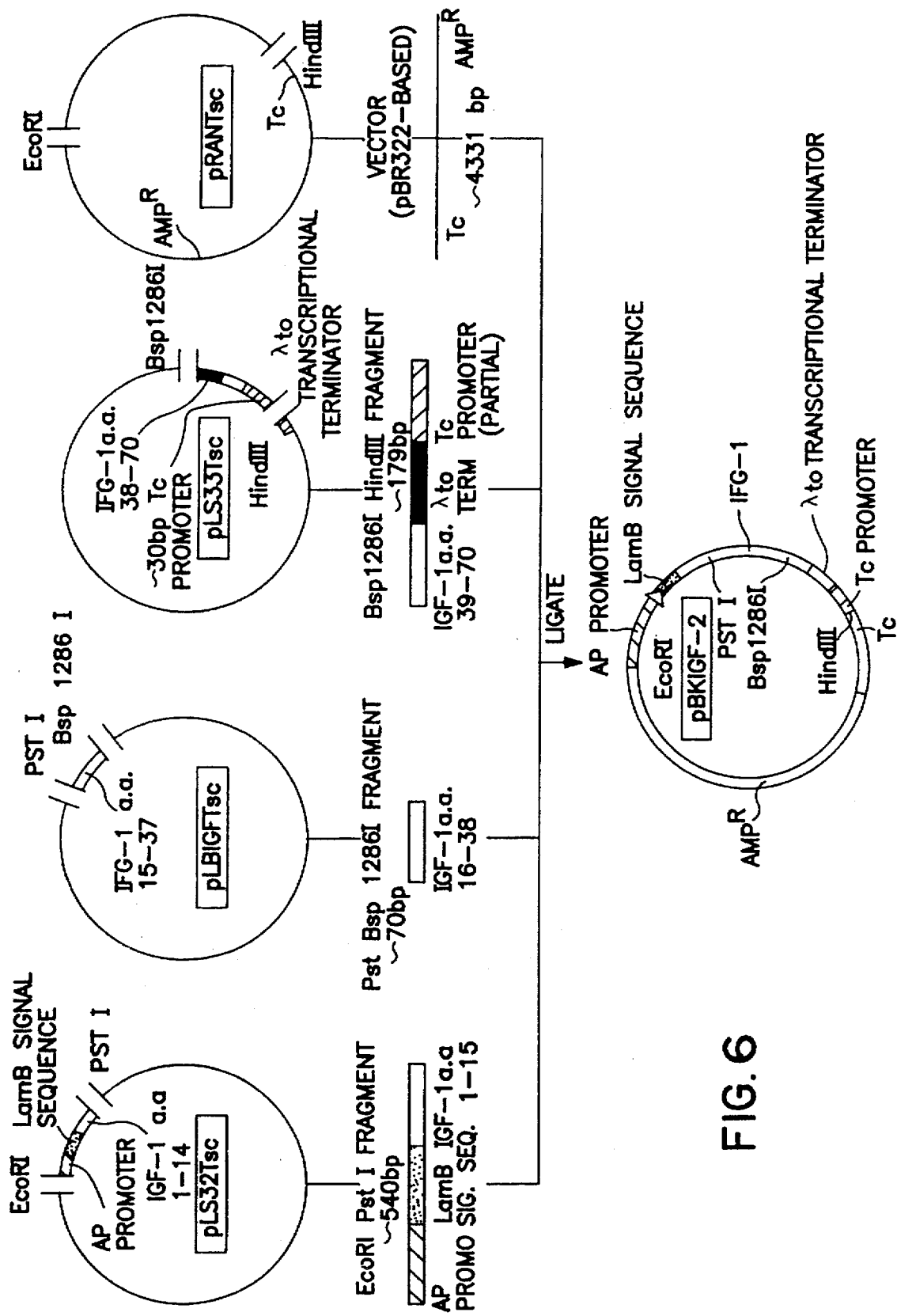
FIG. 6 depicts the construction of pBKIGF-2 from pLS32Tsc, pLBIGFTsc, pLS33Tsc, and pRanTsc.

As shown in FIG. 6, the EcoRI-PstI 540-bp fragment containing the alkaline phosphatase promoters the lamb signal sequence, and DNA encoding the first 15 amino acids of IGF-I was excised from pLS32Tsc. The Pst-Bsp1286I fragment (~70 bp) containing DNA encoding amino acids 16–38 of IGF-I was excised from pLBIGFTsc. The Bsp1286I-HindIII (~179-bp) fragment containing DNA encoding amino acids 39–70 of IGF-I, the lambda terminators and the Tc promoter was excised from pLS33Tsc. Finally, the EcoRI-HindIII ~4331-bp vector fragment (pBR322-based) was excised from pRanTsc. These four fragments were ligated to give pBKIGF-2, which contains the AP promoter, the lamb signal sequence, the DNA encoding the entire IGF-I protein, the transcriptional terminator, the Tc promoter, and the tetracycline and ampicillin resistance markers.

Figure 7:
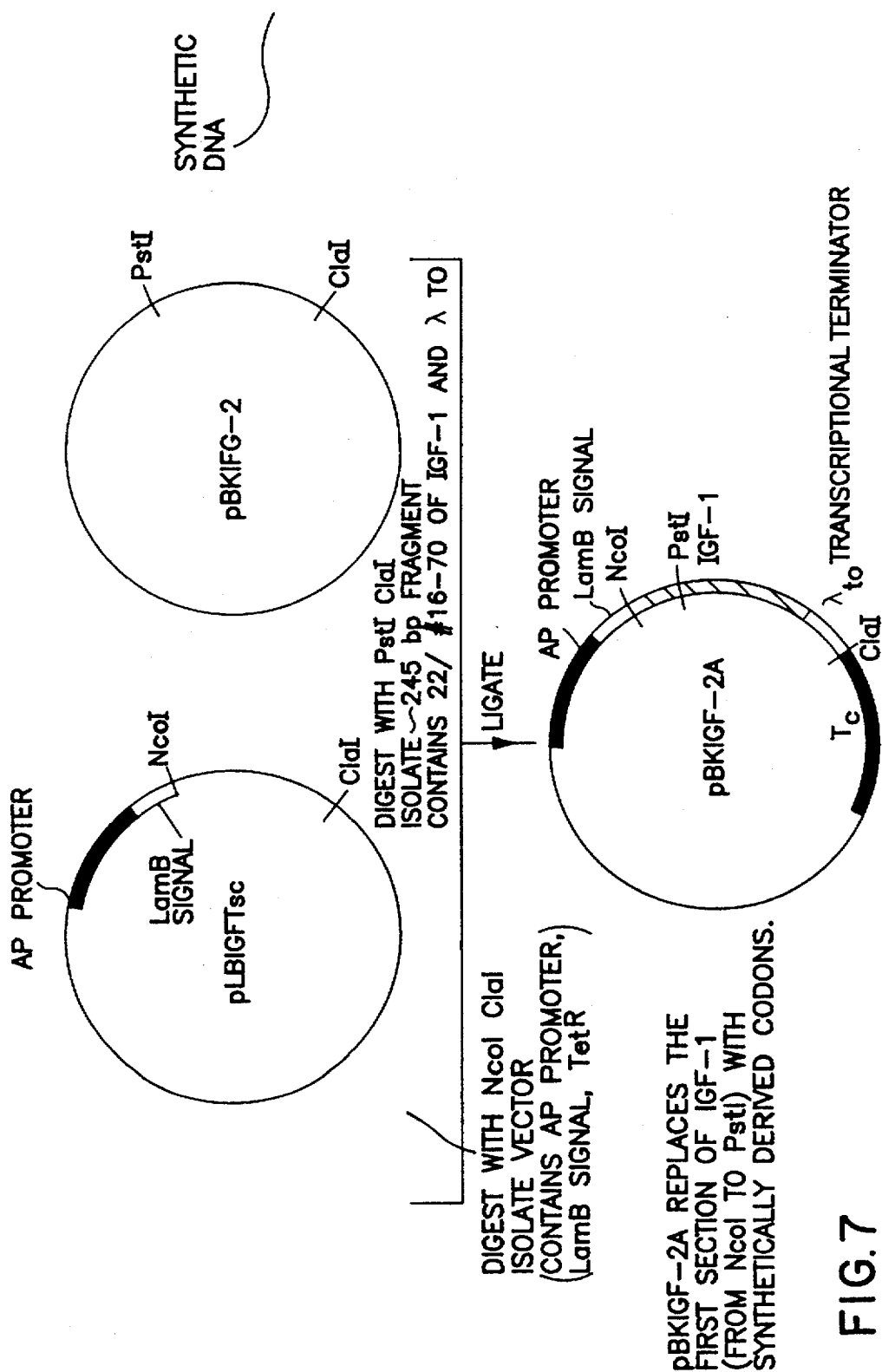
FIG. 7 depicts the construction of pBKIGF-2A, used to prepare pBKIGF-2B, from pLBIGFTsc, pBKIGF-2, and a piece of synthetic DNA (SEQ. ID NOS. 4 and 5).

Step 5: βpBKIGF-2A pBKIGF-2 was digested with PstI and ClaI and the ~245-bp fragment was isolated. This contains amino acids 16–70 of IGF-I and the lambda $t_o$ terminator. pLBIGFTsc was digested with NcoI and ClaI and the vector fragment was isolated. This vector fragment contains the AP promoter, the lamb signal, and the Tet$^r$ gene. These two fragments were ligated to a piece of synthetic DNA that replaces the 5' end of IGF-I DNA from NcoI to PstI with synthetically derived codons as follows:

The resulting plasmid was designated pBKIGF-2A. The construction is shown in FIG. 7.

Step 6: pLamBRan

This plasmid was prepared by digesting pLS33LamB with NcoI and BamHI and the vector fragment was isolated. pLS33LamB is a plasmid made from pBR322 into which was inserted the AP promoters the lamb signal, and the IGF-I gene. BamHI cuts in the Tc portion of the plasmid and NcoI cuts at the 5' end of the IGF-I gene. The second fragment was generated by digesting pRANTES with BsaJI and BamHI and isolating the resultant ~200-bp fragment. The third fragment was a piece of synthetic DNA to link the RANTES gene with the signal sequence from NcoI to BsaJI. This synthetic DNA has the sequence:

```
NcoI                      BsaJI
5'-CATGGCCTCCCCATATTC-3'
      3'-CGGAGGGGTATAAGGAGC-5'
```
(SEQ. ID NOS. 6 and 7, respectively).

Figure 8:
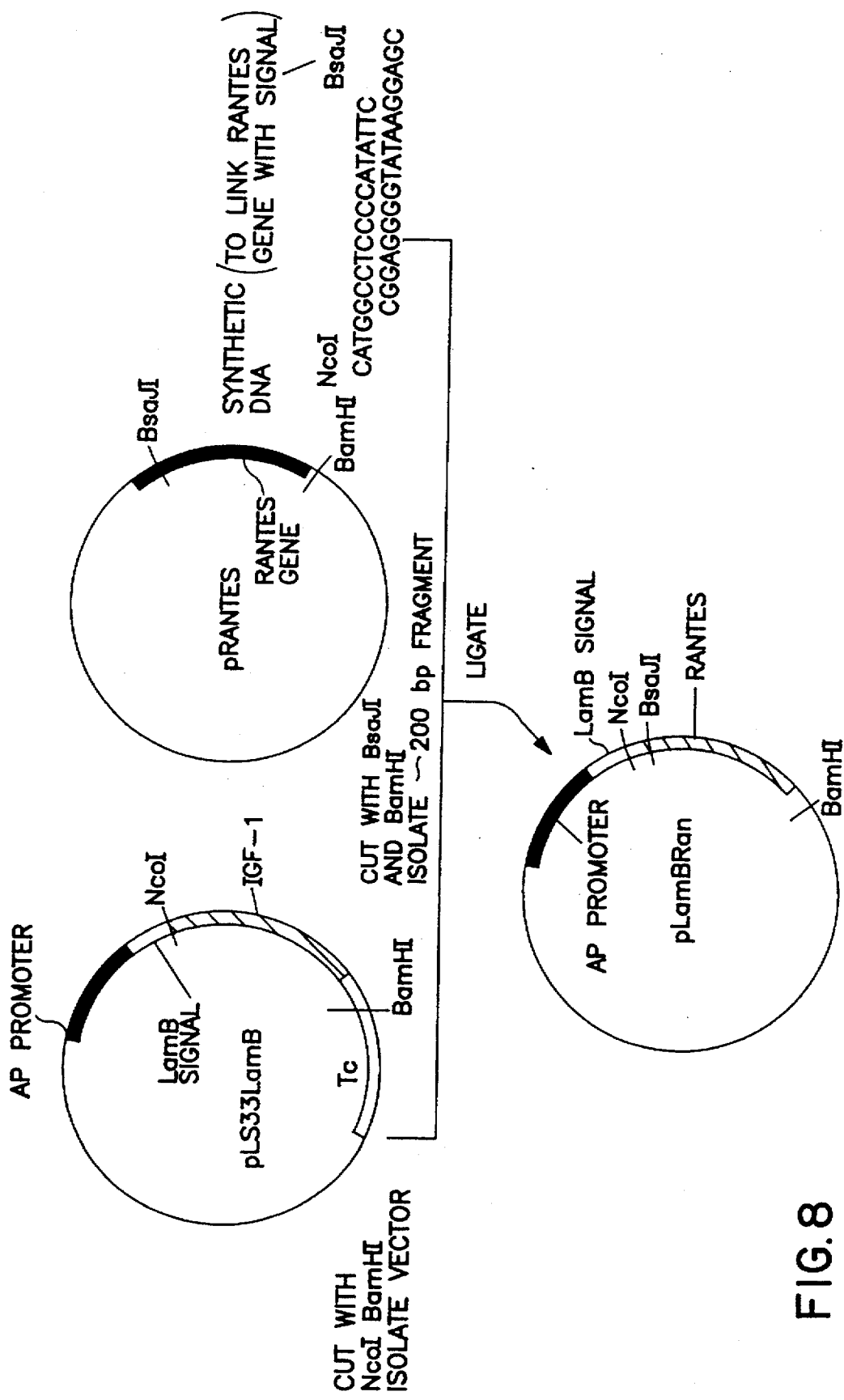
FIG. 8 depicts the construction of pLamBRan, used to prepare pBKIGF-2B, from pLS33LamB, pRANTES and a piece of synthetic DNA (SEQ. ID NOS. 6 and 7).

The resulting vector was named pLamBRan, and its construction is shown in FIG. 8.

Step 7: pBKIGF-2B

Figure 9:
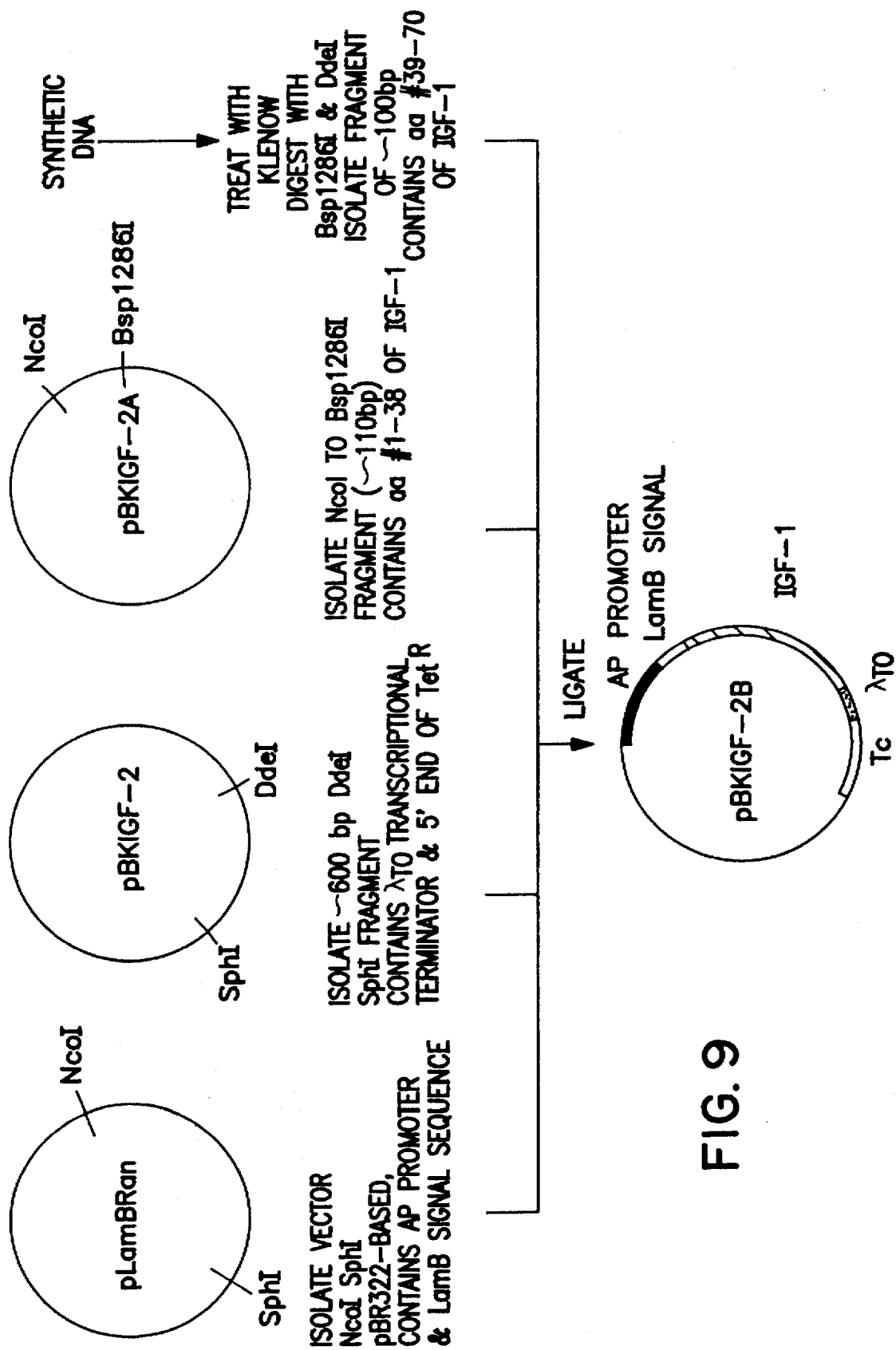
FIG. 9 depicts the construction of expression vector pBKIGF-2B from pBKIGF-2, pBKIGF-2A, pLamBRan, and a piece of synthetic DNA (SEQ. ID NOS. 8 and 9).

The construction of this plasmid is shown in FIG. 9. pLamBRan was digested with NcoI and SphI and the vector fragment was isolated containing the promoter and signal sequence. pBKIGF-2 was digested with DdeI and SphI and the ~600-bp fragment was isolated containing the lambda transcriptional terminator and the 5' end of the $Tet^R$ gene. pBKIGF-2A was digested with NcoI and Bsp1286I and the ~110-bp fragment was isolated containing the DNA encoding amino acids 1–38 of IGF-I. These three fragments were ligated together with synthetic DNA encoding amino acids 39–70 of IGF-I to yield pBKIGF-2B. This synthetic linker has the sequence:

```
5'-TCGTCGTGCTCCC CAG ACT GGT ATT GTT GAC GAA TGC TGC TTT CGT TCT TGC GAC CTG CGT CGT CTG-3'
```
(SEQ. ID NO. 8)

```
                                                                 3'-AGA ACG CTG GAC GCA GCA GAC CTT
TAC ATA ACG CGA GGG GAC TTT GGG CGATTTAGACGAATCTTCGAGG-5'
```
(SEQ. ID NO. 9)

C. Fermentation and Recovery Procedure i. Transformation

Competent *E. coli* 27C7 cells were transformed with pBKIGF-2B by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

ii. Fermentation Inoculum

A 10-L fermentor inoculum was prepared by first inoculating a two-liter shake flask containing approximately 500 mL of sterile LB medium containing tetracycline with the freshly thawed 1–2 mL culture vial described above. This flask was incubated at 35°–39° C. for 8 hours and transferred into a 10-liter fermentor containing the production medium in the range of that described in Section C of this Example. The 10-liter fermentor inoculum was incubated at 35°–39° C. at pH 7.1–7.5 for 6–12 hours. The agitation rate was set at 650–1000 rpm and the aeration rate at 0.7–1.5 volumes of air per volume of culture per minute. The inoculum was then aseptically transferred to a 1000-L fermentation vessel wherein glucose is introduced from the bottom.

The 10-L inoculum was grown like the 500-mL shake flask cultivation to mid-exponential phase (batch cultivation). All the glucose was added to the 10-L fermentor at the start of the fermentation. Only the 1000-L fermentation utilized glucose feeding.

iii. Fermentation Procedure

The 1000-L vessel initially contained 600–800 liters of fermentation medium composed as follows:

| Ingredient | Quantity/Liter |
| --- | --- |
| glucose* | 250–359 g |
| ammonium sulfate | 3–8 g |

-continued

| Ingredient | Quantity/Liter |
| --- | --- |
| ammonium hydroxide | as required to control pH 7.1 to 7.5 |
| sodium phosphate, monobasic dihydrate | 1–2 g |
| potassium phosphate, dibasic | 2–4 g |
| sodium citrate, dihydrate | 0.5–1.5 g |
| potassium chloride | 1–2.5 g |
| 25% Pluronic Polyol L61 | 0.1–0.2 mL initially and as needed to control foaming |
| magnesium sulfate, heptahydrate | 1–3 g |
| tetracycline HCl | 5–20 mg |
| yeast extract** | 5–20 g |
| NZ amine AS** | 5–25 g |
| isoleucine | 0–10 g |
| methionine** | 0–1 g |
| ferric chloride, heptahydrate | 10–30 mg |
| zinc sulfate, heptahydrate | 2–5 mg |
| cobalt chloride, hexahydrate | 2–5 mg |
| sodium molybdate, dihydrate | 2–5 mg |
| cupric sulfate, pentahydrate | 2–5 mg |

-continued

| Ingredient | Quantity/Liter |
| --- | --- |
| boric acid | 0.5–2 mg |
| manganese sulfate, monohydrate | 1–3 mg |

*1–5 g/L of glucose was added to the culture initially. The remainder was fed to the culture over the course of the fermentation.
**Yeast extract, NZ amine AS, and methionine can be added initially and/or fed throughout the fermentation.

The fermentation process was performed at 35°–39° C. at pH 7.1–7.5 for 24–48 hours. The agitation rate was set at 200 rpm and the aeration rate at 0.7–1.5 volumes of air per volume of culture per minute. Production of IGF-I occurred after the phosphate in the medium was depleted. This procedure resulted in fermentation broth containing approximately 18% packed cell volume and over 3 g/L IGF-I, which was principally in the periplasmic space with low levels in the extracellular medium.

D. In-situ Solubilization

At the end of fermentation, all feeds and controllers, with the exception of temperature, were turned off. Temperature control was maintained at 37° C. The sparge was shut off and fermentor back pressure was released. The broth volume was drained to 1200 L and the agitation was lowered from 200 rpm to 150 rpm. The sparge lines and fermentor headspace were then flushed with nitrogen gas, first at a rate of 150 Lpm for 1 minute, then at 50 Lpm for the remainder of the procedure. A 220-L slurry containing 174 kg of urea was then pumped rapidly into the fermentor, followed immediately by approximately 8 L of 50% (w/w) sodium hydroxide, sufficient to adjust the pH to 10.0. A 20-L solution containing 2.9 kg of dithiothreitol was then added and the pH was re-adjusted to 10.0 with approximately 3 additional liters of 50% sodium hydroxide. The batch was held with agitation at 37° C. for 60 minutes, after which it was cooled to 22° C. and transferred to a hold tank for aqueous two-phase extraction. Assays by reversed-phase HPLC showed that the initial titer of IGF-I was 3.8 g/L, and after solubilization IGF-I was quantitatively released from the cells.

E. Aqueous Two-Phase Liquid-Liquid Extraction

The batch temperature was maintained at 22° C. and the tank headspace was flushed with nitrogen. To the treated broth, having a volume of 1450 L, was added 250 kg of PEG-8000 and 90 kg of sodium sulfate. The batch was stirred for approximately 40 minutes. Centrifugation and analysis of samples showed that the phase-volume ratio (Kv) stabilized at 2.6 and the IGF-I distribution coefficient (Kc) was 8.5. The batch was separated using a Westfalia SB-7 separator, yielding approximately 1300 L of light phase and 550 L of heavy phase. Assays by reversed-phase HPLC showed that the isolated light phase contained approximately 88% of the IGF-I in the initial 1450 L of treated broth. The light phase was held under nitrogen and the heavy phase was discarded.

F. Precipitation of IGF-I

Approximately 36 L of 2M phosphoric acid was added to the light phase to adjust the pH to 7.0 at 22° C. The batch was held for approximately 8 hours with gently mixing, at which point assay by reversed-phase HPLC showed that approximately 96% of the IGF-I had precipitated. The pellet was then collected using a Westfalia SB-7 clarifier. The mass of the pellet slurry was approximately 88 kg.

G. Refolding

Figure 10:
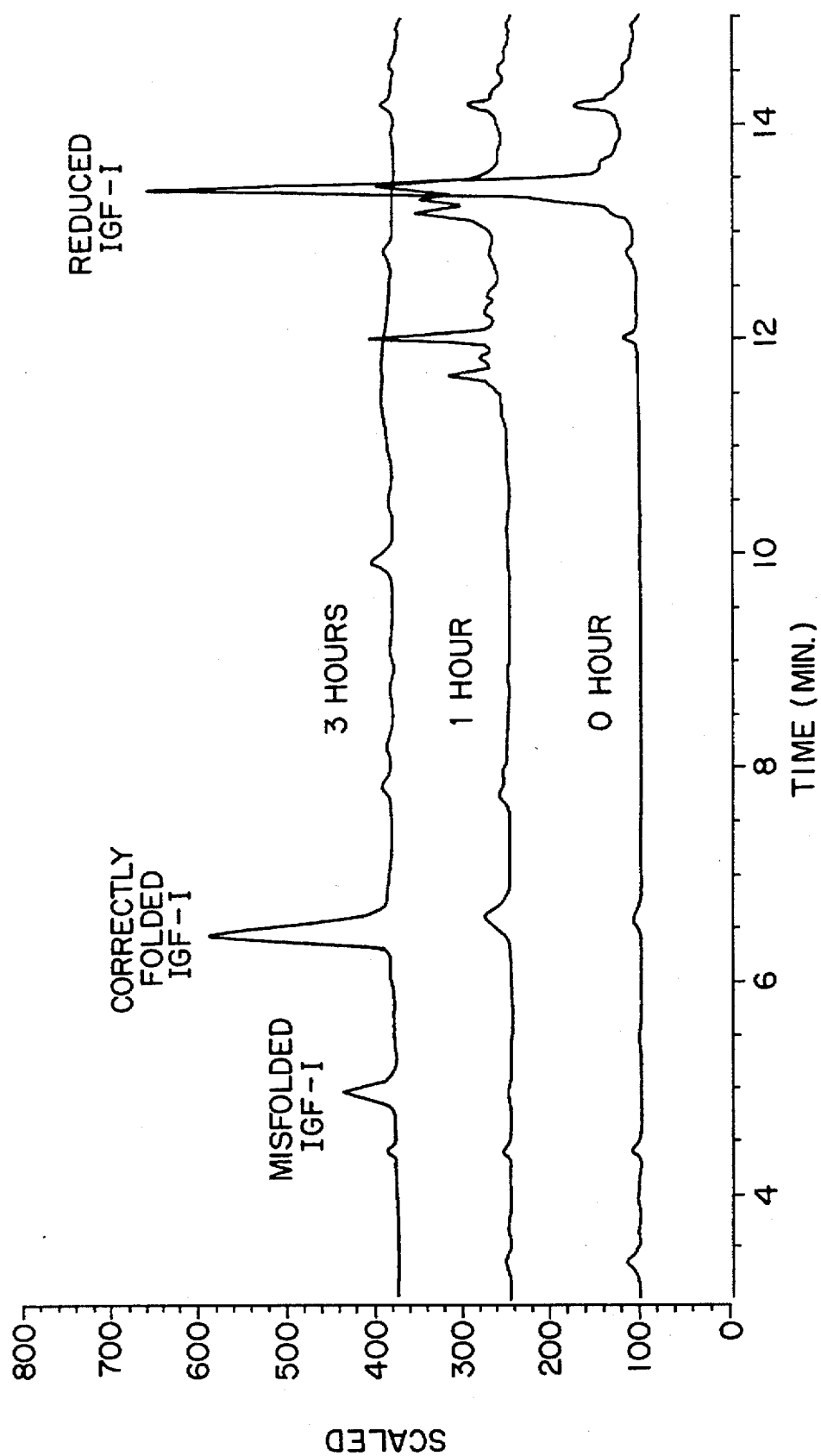
FIG. 10 is a series of three HPLC chromatograms showing the evolution of IGF-I species (from left to right, misfolded IGF-I, correctly folded IGF-I, and reduced IGF-I) during refolding. These chromatograms were taken at initiation of folding (bottom chromatogram), 1 hour after folding began (middle chromatogram), and 3 hours after folding began (top chromatogram).

An aliquot of the pellet slurry, having a mass of 17.6 kg, was dissolved by adding sufficient solid urea to bring the final concentration to 2M, by adding sufficient dithiothreitol to bring the concentration to 10 mM, and by adjusting the pH to 10.0 with 50% (w/w) sodium hydroxide. It was then added to 700 L of folding buffer having a composition of 2M urea, 1M sodium chloride, 19% (v/v) ethanol, 20 mM glycine, 0.5 µM copper, pH 10.5. The final concentration of dithiothreitol was then adjusted to 1 mM. Folding was carried out at 22° C. with gentle mixing by sparging in oxygen gas at 280 mL/minute. The progress of folding was monitored by reversed-phase HPLC. Representative HPLC chromatograms taken at the initiation of, at the middle of, and after termination of folding are shown in FIG. 10. After approximately 3 hours, folding was terminated by cessation of oxygen sparging and by titrating the batch to pH 3.5 with approximately 1.6 L of reagent phosphoric acid. Assay by reversed-phase HPLC showed that the yield of folding was 50%.

EXAMPLE II

The host construction, plasmid construction, and fermentation were carried out as described in Example I, parts A–C. In-situ solubilization was carried out as described in Example I, part D, except that instead of using DTT, the broth was reduced by the addition of sufficient L-cysteine to bring the final concentration to 50 mM (approximately 8.8 kg). At the end of solubilization, assay by reversed-phase HPLC showed that 93% of the IGF-I was released from the cells.

Subsequent isolation was carried out by scaled-down versions of the operations described in Example I, Parts E–G.

EXAMPLE III

Non-native IGF-I was prepared using the host, plasmid, fermentation, and in-situ solubilization procedure described in Example I, parts A–D.

Aqueous two-phase systems were produced using the following procedure: (1) phase-forming species were placed in a graduated 15-ml polystyrene culture tube; (2) 7 mL of whole extract from in-situ solubilization was added, the contents were mixed, and the headspace was flushed with nitrogen; (3) the composition was incubated for two hours at either room temperature or 37° C. with end-over-end mixing. Polymers were added from stock solutions (50% w/w PEG Mr 3350 polymers 50% w/w PEG Mr 8000 polymer, and 100% w/w DOW Polyglycol 15-200™ brand polymer), while salts were added as dry chemicals. Components were added to achieve a predetermined composition on a weight-to-weight basis, assuming that whole extract has a density of 1 g/mL.

Phases were separated by centrifugation at either 25° C. or 37° C. at about 1300 g for 20 minutes. The concentration of IGF-I in the top phase was determined by reversed-phase HPLC analysis. The concentration of IGF-I in the bottom phase was calculated using a mass balance assumption.

Three experiments were conducted in which the concentration and type of phase-forming polymer, concentration and type of phase-forming salt, concentration and type of non-phase-forming salt, and temperature were varied. Resulting systems could be visually characterized as belonging in one of the five categories listed: (1) one-phase systems, (2) two-phase systems in which solids sediment in the bottom phase, (3) two-phase systems in which some solids float in the bottom phase, (4) two-phase systems in which solids are distributed throughout both the top and bottom phases, and (5) two-phase systems in which solids are distributed in the top phase.

Figure 11:
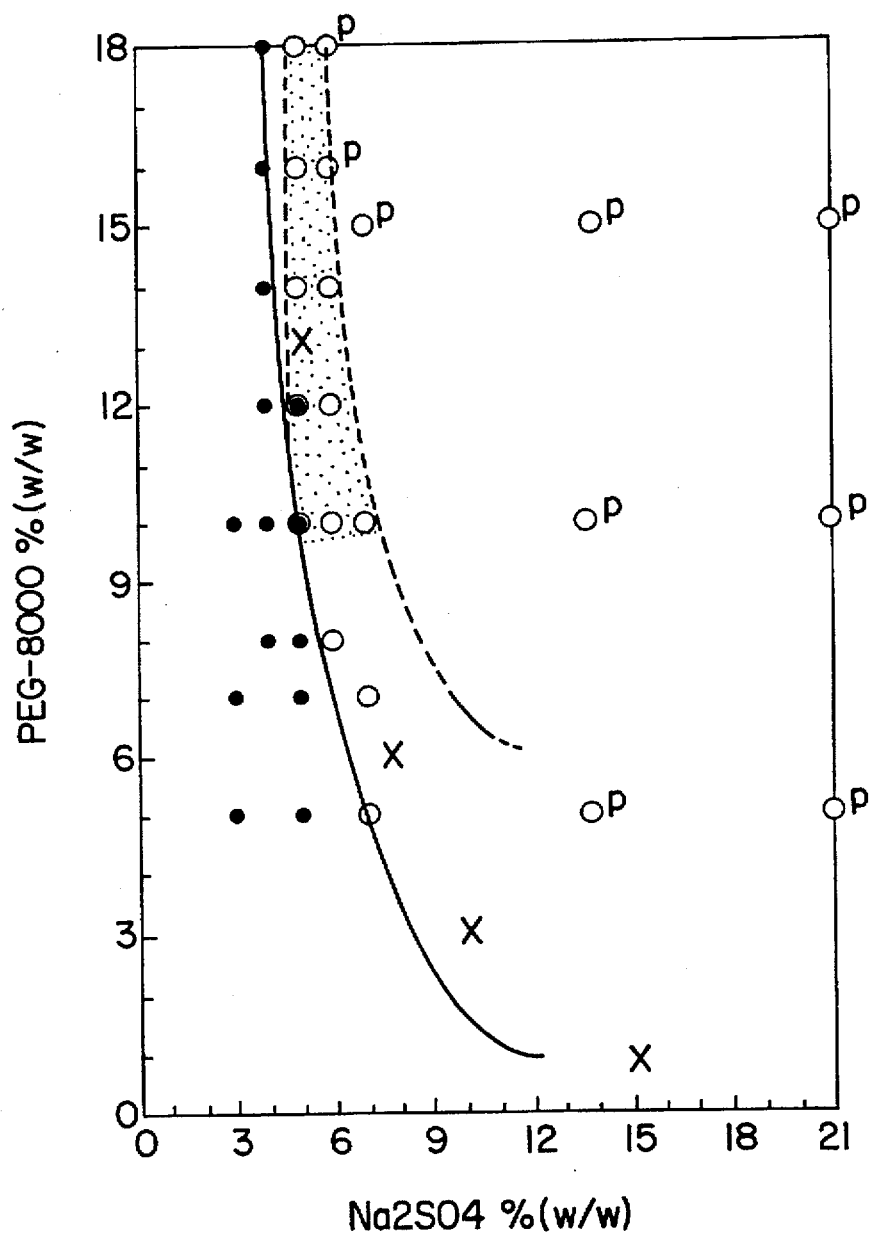
FIG. 11 is a phase diagram describing aqueous two-phase systems produced by adding salt and polymer to whole extract containing urea, DTT, non-native IGF-I, and cell-associated solids. Symbols are used to indicate two-phase systems (open circles), one-phase systems (filled circles), two-phase systems with floating solids (ρ), and published binodal points (X). Curves are used to show the approximate position of the binodal (solid), the limit for solid sedimentation (dashed), and the phase ratio limit allowing lower phase containment of solids (dotted). The shaded region indicates the optimum region for separation of IGF-I and cell-associated solids.

The plot shown in FIG. 11 illustrates this relationship between system composition and disposition for systems composed only of whole extract, PEG-8000, and $Na_2SO_4$. In this plot, "two-phase systems with floating solids" indicates all two-phase systems in which solids do not sediment in the bottom phase. The plot also indicates the limit describing systems in which solids are sedimented in a lower phase that is just large enough to accommodate their volume. The most preferable systems in which solids sediment in the bottom phase, the lower-phase volume is sufficient to accommodate solids, and the phase-volume ratio is greater than about 1 are contained within the shaded region.

These three experiments also provided data that allow the different aqueous two-phase systems to be quantitatively compared as shown in Table I. To reduce error and allow the effect of a given change to be more apparent, volume ratio and partition coefficient data were averaged for several different systems as indicated. Results from this analysis indicate several trends. The polymers PEG-8K and PEG-4K (having Mr values of 8000 and 3350, respectively) form systems having similar volume ratios in which non-native IGF-I partitions similarly. Including NaCl in examined phase systems does not affect the volume ratio but does decrease the IGF-I partition coefficient. Adding the random polyethylene glycol, polypropylene glycol copolymer DOW Polyglycol 15-200™ brand polymer (Mr~2500) does not alter the volume ratio or partition coefficient. Including the phase-forming salt citrate in PEG-8000 and $Na_2SO_4$ systems shifts the position of the binodal curve but does not affect IGF-I partitioning. Conducting aqueous two-phase extraction at 37° C. decreases the volume ratio and partition coefficient relative to 25° C.

TABLE I

Averaged Effect of Aqueous Two-Phase Effectors on Kv and Kc

| Condition | n | Kv | Kc | Averaged Over |
|---|---|---|---|---|
| Experiment #1 | | | | |
| 7% Na$_2$SO$_4$/PEG-8K | 6 | 1.09 | 2.5 | [PEG] = 10, 15% (w/w) |
| 7% Na$_2$SO$_4$/PEG-4K | 6 | 0.99 | 2.7 | [NaCl] = 0, 3, 6% (w/w) |
| Experiment #1 | | | | |
| 7% Na$_2$SO$_4$ | 4 | 1.03 | 2.9 | [PEG] = 10, 15% (w/w) |
| 7% Na$_2$SO$_4$, 6% NaCl | 4 | 1.06 | 2.3 | PEG Mr = 4, 8 kD |
| Experiment #2 | | | | |
| 7% Na$_2$SO$_4$/PEG-8K | 9 | 0.58 | 1.6 | [PEG-8K] = 5, 7, 10% (w/w) |
| 7% Na$_2$SO$_4$/PEG-8K + | 9 | 0.57 | 1.5 | [NaCl] = 0, 3% (w/w) |
| 2% EP15-200 | | | | [Citrate] = 0, 3% (w/w) |
| **Experiment #2 | | | | |
| 7% Na$_2$SO$_4$ | 6 | 0.60 | 1.6 | [PEG-8K] = 5, 7, 10% (w/w) |
| 5% Na$_2$SO$_4$, 3% citrate | 6 | 0.60 | 1.5 | [EP15-200] = 0, 2% (w/w) |
| Experiment #3 | | | | |
| 25° C. | 6 | 1.95 | 2.0 | [PEG-8K] = 12, 14, 16% (w/w) |
| 37° C. | 6 | 1.76 | 1.8 | [Na$_2$SO$_4$] = 5, 6% (w/w) |

**Data were averaged in a manner to account for changes in the position of the binodal curve.

EXAMPLE IV

Non-native IGF-I was prepared using the host, plasmid, fermentation, and in-situ solubilization procedure described in Example I, parts A–D.

Aqueous two-phase systems were produced as described in Example III with the exception that PEG-8000 was added in dry form rather than as a stock solution. The concentrations of IGF-I in the top phase and bottom liquid phase were determined by reversed-phase HPLC analysis. The bottom liquid phase was subjected to 0.2 μm filtration prior to analysis to remove residual suspended solids.

Results of direct determination of the partition coefficient of non-native IGF-I in aqueous two-phase systems are shown in Table II. With a condition of 5% (w/w) Na$_2$SO$_4$, 14% (w/w) PEG-8000, the distribution coefficient has a magnitude of 9 to 10. A 1% (w/w) increase in the salt concentration or a 2% (w/w) increase in the polymer concentration doubles its magnitude. Combined increases in the salt and polymer concentrations lead to a four-fold increase, resulting in a value near 40. This latter combination results in formation of a two-phase system with floating solids.

TABLE II

Partition Coefficient of Whole-Extract IGF-I
in PEG-8000, Na$_2$SO$_4$ Aqueous Two-Phase Systems

| Na$_2$SO$_4$ | PEG-8K (% w/w) | | |
|---|---|---|---|
| (% w/w) | 12 | 14 | 16 |
| 5 | 1-phase | 9.0 | 19.1 |
| | | 2.38 | 2.04 |
| | | 96 | 98 |
| 6 | 12.0 | 21.9 | 41 |
| | 1.29 | 1.31 | 1.24 |
| | 94 | 97 | 98 |

Values indicate, from top to bottom, respectively: IGF-I distribution coefficient (measured), phase-volume ratio, and mass percentage of soluble whole-extract IGF-I in top phase.

EXAMPLE V

Non-native IGF-I was prepared using the fermentation, in situ solubilization, and aqueous two-phase extraction procedures as described in Example I, Parts A–E. For IGF-I precipitation, a portion of the light phase was divided into several aliquots that were then titrated to approximately pH 6 using one of the following acids: 2N phosphoric, 2N acetic, 2N sulfuric, 2N hydrochloric, 2N citric, or 2N nitric acid. The aliquots were then centrifuged briefly at approximately 5000×g for 15 minutes and the supernatant liquids were decanted. Assays by reversed-phase HPLC showed that, in all cases, at least 93% of the starting IGF-I was recovered in the pellet. Subsequent protein folding of pellets was carried out by a scaled-down version of the procedure described in Example I, Part G.

EXAMPLE VI

Non-native IGF-I was prepared using the fermentation, in situ solubilization, and aqueous two-phase extraction procedures as described in Example I, Parts A–E.

A sample of the light phase from part E of Example I was divided into several smaller aliquots, and acid precipitation was initiated by titrating these aliquots to either pH 10, 4.5, 4.0, 3.5, or 3.0 using 2M sulfuric acid. Each of these five stocks was then further divided into five aliquots, which received solid sodium sulfate sufficient to give a final concentration of either 3, 4, 5, 6, or 7% by weight. The samples were incubated for two hours at 25° C. with gentle mixing. The phases were then separated after centrifugation at approximately 5000×g for 20 minutes. The concentration of IGF-I in both phases was assayed by reversed-phase HPLC.

For all sodium sulfate levels at pH 10, greater than 95% of the IGF-I remained in the top phase. For all samples at all other pHs (4.5 to 3.0), greater than 98% of the IGF-I was recovered in the bottom phase.

EXAMPLE VII

Non-native IGF-I was prepared using the fermentation, in-situ solubilization, aqueous two-phase extraction, and neutralization precipitation procedure described in Example 1, Parts A–G.

A suspension containing reduced IGF-I was prepared from IGF-I pellet obtained by neutralization precipitation. To produce this suspension 30 g of wet pellet containing IGF-I was resuspended in a solution containing 20 mM glycine (pH 10.5), 2M urea, and 10 mM DTT to a final volume of 100 mL. The pH of the resulting suspension was adjusted to pH 10.5 by addition of NaOH and HCl as required. Reversed-phase HPLC analysis of the suspension indicated that it contained 35 mg/mL IGF-I.

Refolding buffers were prepared in 15-mL polystyrene culture tubes by addition of appropriate amounts of the following stock solutions: 1M glycine (pH 10.5) and 25 μM CuCl$_2$, 9M urea, 100% ethanol, 1.8M Na$_2$SO$_4$, 20% (v/v) PEG-3350, and 20% (v/v) PEG-8000. Each tube received 0.1 mL of the 50× buffer stock solution containing glycine and CuCl$_2$. Other stocks were added so as to have the indicated concentration at a final volume of 5 mL. Each tube containing refolding buffer components was brought to a final volume of 4 mL.

IGF-I refolding was initiated by diluting 1 mL of reduced IGF-I suspension into the previously prepared refolding buffers, giving an initial IGF-I concentration of 7 mg/mL. Tubes were capped and shaken horizontally on an orbital shaker. Each tube contained 5 mL of liquid and 10 mL of air. Refolding was allowed to occur for three hours after which samples were collected, diluted by a factor of 10 into an acidified buffer containing 20 mM glycine (pH 3), 2M urea, and analyzed by reversed-phase HPLC to determine the content of correctly folded IGF-I.

The object of this example is to show the effect of aqueous phase-forming components on yield of correctly folded IGF-I obtained during refolding. The specific phase-forming components investigated were $Na_2SO_4$, PEG-3350, PEG-8000, and ethanol. The concentrations examined were consistent with those which may be produced by diluting an isolated aqueous phase by a factor of 10 to 15.

Results, shown in Table III, indicate that yield of correctly folded IGF-I is enhanced by refolding IGF-I in the presence of the phase-forming components ethanol and $Na_2SO_4$. Yield of IGF-I is not affected by the presence of the phase-forming components PEG-3350 or PEG-8000.

TABLE III

Effect of Aqueous Phase-Forming Species on IGF-I Refolding Yield

| $Na_2SO_4$ (M) | No PEG | PEG-3350 0.88% (w/w) | PEG-8000 1.05% (w/w) |
|---|---|---|---|
| | | No Ethanol | |
| 0   | 11.4% | 11.6% | 11.3% |
| 0.1 | 11.9% | 11.6% | 11.4% |
| 0.3 | 9.4%  | 9.7%  | 9.3%  |
| 0.6 | 4.4%  | 4.0%  | 3.8%  |
| | | 20% (v/v) Ethanol | |
| 0   | 22.7% | 23.0% | 23.6% |
| 0.1 | 25.7% | *     | 23.2% |
| 0.3 | 28.4% | 28.3% | 28.3% |
| 0.6 | 26.4% | 25.8% | 25.8% |

The initial concentration of IGF-I was 7 mg/mL.

EXAMPLE VIII

Non-native IGF-I was prepared using the fermentation, in-situ solubilization, aqueous two-phase extraction, and neutralization precipitation procedures described in Example I, Parts A–G.

A suspension containing reduced IGF-I was prepared from IGF-I pellet obtained by neutralization precipitation. To produce this suspension, 10 g of wet pellet containing IGF-I was resuspended in 45 mL of a solution containing 20 mM glycine (pH 10.5), 2M urea, and 10 mM DTT. The pH of the resulting suspension was adjusted to pH 10.5 by addition of NaOH as required. Reversed-phase HPLC analysis of the pH-adjusted suspension indicated that it contained 15 mg/mL IGF-I. The pH-adjusted suspension was spiked with a concentrated DTT solution to obtain a final DTT concentration of 15 mM. The resulting reduced IGF-I suspension contained 15 mg/mL IGF-I, 20 mM glycine (pH 10.5), 2M urea, and 15 mM DTT.

Refolding buffers were prepared in 15-mL polystyrene culture tubes by addition of appropriate amounts of various stock solutions and dry chemicals. Each tube received 0.1 mL of a 50× buffer stock solution containing 1M glycine (pH 10.5), and 25 µM $CuCl_2$. Appropriate amounts of other chemicals were added so as to have the indicated concentration at a final volume of 5 mL. Ethanol and glycerol were added as liquids. Urea, NaCl, and $Na_2SO_4$ were added in dry form. Each tube containing refolding buffer components was brought to a final volume of 4.7 or 3.7 mL depending on whether refolding was to be conducted at 1 or 4 mg/mL IGF-I, respectively.

IGF-I refolding was initiated by diluting 0.3 or 1.3 mL of reduced IGF-I suspension, for refolding at 1 or 4 mg/mL IGF-I, respectively; into the previously prepared refolding buffers. Tubes were capped and shaken horizontally on an orbital shaker. Each tube contained 5 mL of liquid and 10 mL of air. Refolding was allowed to occur for 8 hours after which samples were collected, acidified, and analyzed by reversed-phase HPLC to determine the content of correctly folded IGF-I.

The following aspects of refolding buffer composition were investigated: salt type and concentration (0, 0.5, 1.0M NaCl; or 0, 0.2, 0.6M $Na_2SO_4$), chaotrope concentration (1, 2, 3M urea), solvent concentration (0, 10, 20% v/v ethanol), osmolyte concentration (0, 20, 30% v/v glycerol), and initial IGF-I concentration (1, 4 mg/mL). The yields obtained with select combinations of these components are shown in Table IV. Inspection shows that the highest yield of correctly folded IGF-I was obtained by refolding at the following condition: 1 mg/mL IGF-I, 20 mM glycine (pH 10.5), 2M urea, 1M NaCl, 20% (v/v) ethanol, and 0.5 µM $CuCl_2$ (sample #0).

The experiment described in this example was designed to allow multifactorial statistical analysis of correctly folded IGF-I yield data in order to assess the importance of all single factors and all two-factor interactions. The results from this statistical analysis are shown in Tables V and VI. Inspection of these results shows that, under the experimental conditions employed, the following trends were apparent: (1) best yields are obtained by refolding at low IGF-I concentration; (2) including salt at a concentration of about 1M improves refolding yield particularly in the presence of ethanol; (3) NaCl is a more preferred salt than is $Na_2SO_4$; (4) better yield is obtained with refolding in 2–3M urea relative to lower urea concentration, although the difference is diminished in the presence of ethanol; (5) improved yield is obtained in the presence of 20% (v/v) ethanol relative to absence of solvent; and (6) including glycerol improves yield but its advantage is reduced in the presence of ethanol.

TABLE IV

Effect of Solution Conditions on IGF-I Refolding Yield

| Sample # (%) | Salt | [Salt] (M) | [IGF-I] (mg/mL) | [urea] (M) | [ethanol] % (v/v) | [glycerol] (v/v) | Yield IGFI |
|---|---|---|---|---|---|---|---|
| 0  | NaCl      | 1   | 1 | 2 | 20 | 0  | 50 |
| 1  | NaCl      | 1   | 1 | 3 | 20 | 30 | 39 |
| 2  | NaCl      | 1   | 1 | 3 | 0  | 0  | 33 |
| 3  | NaCl      | 0   | 1 | 3 | 20 | 0  | 38 |
| 4  | NaCl      | 0   | 1 | 3 | 0  | 30 | 34 |
| 5  | NaCl      | 1   | 1 | 1 | 20 | 0  | 49 |
| 6  | NaCl      | 1   | 1 | 1 | 0  | 30 | 36 |
| 7  | NaCl      | 0   | 1 | 1 | 20 | 30 | 34 |
| 8  | NaCl      | 0   | 1 | 1 | 0  | 0  | 23 |
| 9  | NaCl      | 0.5 | 1 | 2 | 10 | 20 | 44 |
| 10 | NaCl      | 0.5 | 1 | 2 | 10 | 20 | 45 |
| 11 | NaCl      | 1   | 4 | 3 | 20 | 0  | 33 |
| 12 | NaCl      | 1   | 4 | 3 | 0  | 30 | 27 |
| 13 | NaCl      | 0   | 4 | 3 | 20 | 30 | 24 |
| 14 | NaCl      | 0   | 4 | 3 | 0  | 0  | 15 |
| 15 | NaCl      | 1   | 4 | 1 | 20 | 30 | 31 |
| 16 | NaCl      | 1   | 4 | 1 | 0  | 0  | 7  |
| 17 | NaCl      | 0   | 4 | 1 | 20 | 0  | 21 |
| 18 | NaCl      | 0   | 4 | 1 | 0  | 30 | 19 |
| 19 | NaCl      | 0.5 | 4 | 2 | 10 | 20 | 30 |
| 20 | NaCl      | 0.5 | 4 | 2 | 10 | 20 | 31 |
| 21 | $Na_2SO_4$ | 0.6 | 1 | 3 | 20 | 0  | 32 |
| 22 | $Na_2SO_4$ | 0.6 | 1 | 3 | 0  | 30 | 36 |
| 23 | $Na_2SO_4$ | 0   | 1 | 3 | 20 | 30 | 31 |
| 24 | $Na_2SO_4$ | 0   | 1 | 3 | 0  | 0  | 28 |
| 25 | $Na_2SO_4$ | 0.6 | 1 | 1 | 20 | 30 | 37 |
| 26 | $Na_2SO_4$ | 0.6 | 1 | 1 | 0  | 0  | 11 |
| 27 | $Na_2SO_4$ | 0   | 1 | 1 | 20 | 0  | 36 |

TABLE IV-continued

Effect of Solution Conditions on IGF-I Refolding Yield

| Sample # (%) | Salt | [Salt] (M) | [IGF-I] (mg/mL) | [urea] (M) | [ethanol] % (v/v) | [glycerol] (v/v) | Yield IGFI |
|---|---|---|---|---|---|---|---|
| 28 | Na$_2$SO$_4$ | 0 | 1 | 1 | 0 | 30 | 29 |
| 29 | Na$_2$SO$_4$ | 0.2 | 1 | 2 | 10 | 20 | 45 |
| 30 | Na$_2$SO$_4$ | 0.2 | 1 | 2 | 10 | 20 | 45 |
| 31 | Na$_2$SO$_4$ | 0.6 | 4 | 3 | 20 | 30 | 29 |
| 32 | Na$_2$SO$_4$ | 0.6 | 4. | 3 | 0 | 0 | 9 |
| 33 | Na$_2$SO$_4$ | 0 | 4 | 3 | 20 | 0 | 26 |
| 34 | Na$_2$SO$_4$ | 0 | 4 | 3 | 0 | 30 | 24 |
| 35 | Na$_2$SO$_4$ | 0.6 | 4 | 1 | 20 | 0 | 29 |
| 36 | Na$_2$SO$_4$ | 0.6 | 4 | 1 | 0 | 30 | 12 |
| 37 | Na$_2$SO$_4$ | 0 | 4 | 1 | 20 | 30 | 24 |
| 38 | Na$_2$SO$_4$ | 0 | 4 | 1 | 0 | 0 | 9 |

TABLE V

Average Yield of Correctly Folded IGF-I by Refolding Solution Component

A. By Initial IGF-I Concentration

| [IGF-I] (mg/mL) | Yield IGF-I (%) |
|---|---|
| 1.0 | 32.9 |
| 4.0 | 21.2 |

B. By Salt Type

| Salt | Yield IGF-I (%) |
|---|---|
| NaCl | 29.1 |
| Na$_2$SO$_4$ | 25.1 |

C. By Salt Level

| Salt Level | Yield IGF-I (%) |
|---|---|
| None | 26.0 |
| High | 28.2 |

D. By Urea Concentration

| [Urea] (M) | Yield IGF-I (%) |
|---|---|
| 1.0 | 25.4 |
| 3.0 | 28.8 |

E. By Ethanol Concentration

| [Ethanol] (% v/v) | Yield IGF-I (%) |
|---|---|
| 0.0 | 22.1 |
| 20.0 | 32.0 |

F. By Glycerol Concentration

| [Glycerol] (% v/v) | Yield IGF-I (%) |
|---|---|
| 0.0 | 24.9 |
| 30.0 | 29.3 |

TABLE VI

Average Yield of Correctly Folded IGF-I by Refolding Solution Component Combinations A. By Ethanol and Glycerol Concentration

| | No Glycerol | 30% Glycerol |
|---|---|---|
| No Ethanol | 16.9 | 27.3 |
| 20% Ethanol | 32.9 | 31.2 |

B. By Ethanol and Urea Concentration

| | 1 M Urea | 3 M Urea |
|---|---|---|
| No Ethanol | 18.3 | 25.9 |
| 20% Ethanol | 32.5 | 31.6 |

C. By Ethanol and Salt Concentration

| | No Salt | High Salt |
|---|---|---|
| No Ethanol | 22.9 | 21.4 |
| 20% Ethanol | 29.2 | 34.9 |

D. By Salt Type and Salt Level

| | No Salt | High Salt |
|---|---|---|
| NaCl | 26.1 | 32 |
| Na$_2$SO$_4$ | 25.9 | 24.3 |

EXAMPLE IX

A reduced IGF-I stock solution was prepared from highly purified, correctly folded IGF-I. A solution containing 1 mg/mL IGF-I, 20 mM glycine (pH 10.5), 2 mM citrate, 0.1M NaCl, and 2M urea was placed in a stoppered vial and the headspace was flushed with humidified argon gas for about one hour with occasional swirling. Following solution deoxygenation, DTT was added via syringe from a 117 mM stock solution to a final concentration of 1.17 mM. Following DTT addition, the solution was incubated for two hours with continued argon headspace flushing.

Refolding solutions were prepared from a common buffer stock solution containing 20 mM glycine (pH 10.5); 0.1M NaCl, and 2M urea. This buffer stock was dispensed in vials and CuCl$_2$, NiCl$_2$, ZnCl$_2$, CoCl$_2$, MnCl$_2$, and FeCl$_3$ were added separately from 1.3 mM stock solutions. Vials containing resulting solutions were stoppered, and the liquid was sparged continuously with either humidified argon or oxygen.

To initiate a refolding reaction, an aliquot of reduced IGF-I stock solution was rapidly diluted by a factor of 10 into a refolding solution. The reduced IGF-I stock solution was transferred via syringe to initiate refolding. Control refolding reactions (lacking transition metal salt) and test refolding reactions were conducted simultaneously and shared a common gas source.

Samples were collected by syringe from refolding reactions after 18 minutes of oxidation and rapidly added to septum-covered microvials containing a small amount of 6N HCl. The extent of IGF-I refolding was determined by analyzing samples by reversed-phase HPLC.

As shown in Table VII, exposing reduced IGF-I to oxygen in the presence of either CuCl$_2$ or MnCl$_2$ led to both oxidation of reduced IGF-I and formation of correctly folded IGF-I. The presence of CoCl$_2$ led to oxidation of reduced IGF-I but formation of less correctly folded IGF-I. Both NiCl$_2$ and FeCl$_3$ resulted in yet less oxidation of reduced IGF-I and formation of correctly folded IGF-I. The response to ZnCl$_2$ was not different from that to trace elements.

TABLE VII

Oxidation Catalysis with Various Transition Metal Ions

| Condition | % Correctly Folded IGF-I | % Reduced IGF-I Remaining |
|---|---|---|
| Argon, trace | 0 | 77 |
| $O_2$, trace | 0 | 59 |
| $O_2$, 13 μM $CuCl_2$ | 13 | 0 |
| $O_2$, 13 μM $NiCl_2$ | 1.5 | 37 |
| $O_2$, 13 μM $ZnCl_2$ | 0 | 61 |
| $O_2$, 13 μM $CoCl_2$ | 2.3 | 3.8 |
| $O_2$, 13 μM $MnCl_2$ | 11 | 3.3 |
| $O_2$, 13 μM $FeCl_3$ | 1.6 | 29 |

EXAMPLE X

A reduced IGF-I stock solution was prepared from highly purified, correctly folded IGF-I as described in Example IX.

Refolding solutions were prepared from a common buffer stock solution containing 20 mM glycine (pH 10.5), 0.1M NaCl, and 2M urea. This buffer stock was dispensed in vials and $CuCl_2$ was added separately as required from 1.3, 0.13, 0.013, and 0.0013 mM stock solutions that had been previously prepared by serial dilution. After $CuCl_2$ was added, vials were stoppered and the liquid was sparged continuously with either humidified argon or oxygen.

To initiate a refolding reaction, an aliquot of reduced IGF-I stock solution was rapidly diluted by a factor of ten into a refolding solution. The reduced IGF-I stock solution was transferred via syringe to initiate refolding. Control refolding reactions (lacking $CuCl_2$) and test refolding reactions were conducted simultaneously and shared a common gas source.

Samples were collected by syringe from refolding reactions at predetermined intervals and rapidly added to septum-covered microvials containing a small amount of 6N HCl. This treatment lowers the pH of the sample to pH 3 and effectively quenches the refolding reaction. Samples were collected and quenched at the following times post-refolding initiation: 0, 2, 4, 6, 10, 20, 40, 60, 100, and 200 minutes. The extent of IGF-I refolding with time was determined by analyzing time-course samples by reversed-phase HPLC.

The following concentrations of $CuCl_2$ were investigated: tracer 0.013 μM, 0.052 μM, 0.13 μM, 0.52 μM, 1.3 μM, 5.2 μM, and 13 μM $CuCl_2$. A plot of the evolution of correctly folded IGF-I during aerobic oxidation catalysis at these $CuCl_2$ concentrations is shown in FIG. 12.

Results show that during aerobic oxidation catalysis, a low $CuCl_2$ concentration (between about 0.05 μM and 15 μM, preferably between 0.05 and 0.5 μM) provides higher yield of correctly folded polypeptide than higher concentrations (greater than about 15 μM) and provides more rapid and reproducible oxidation kinetics than trace-element catalysis.

Figure 12:
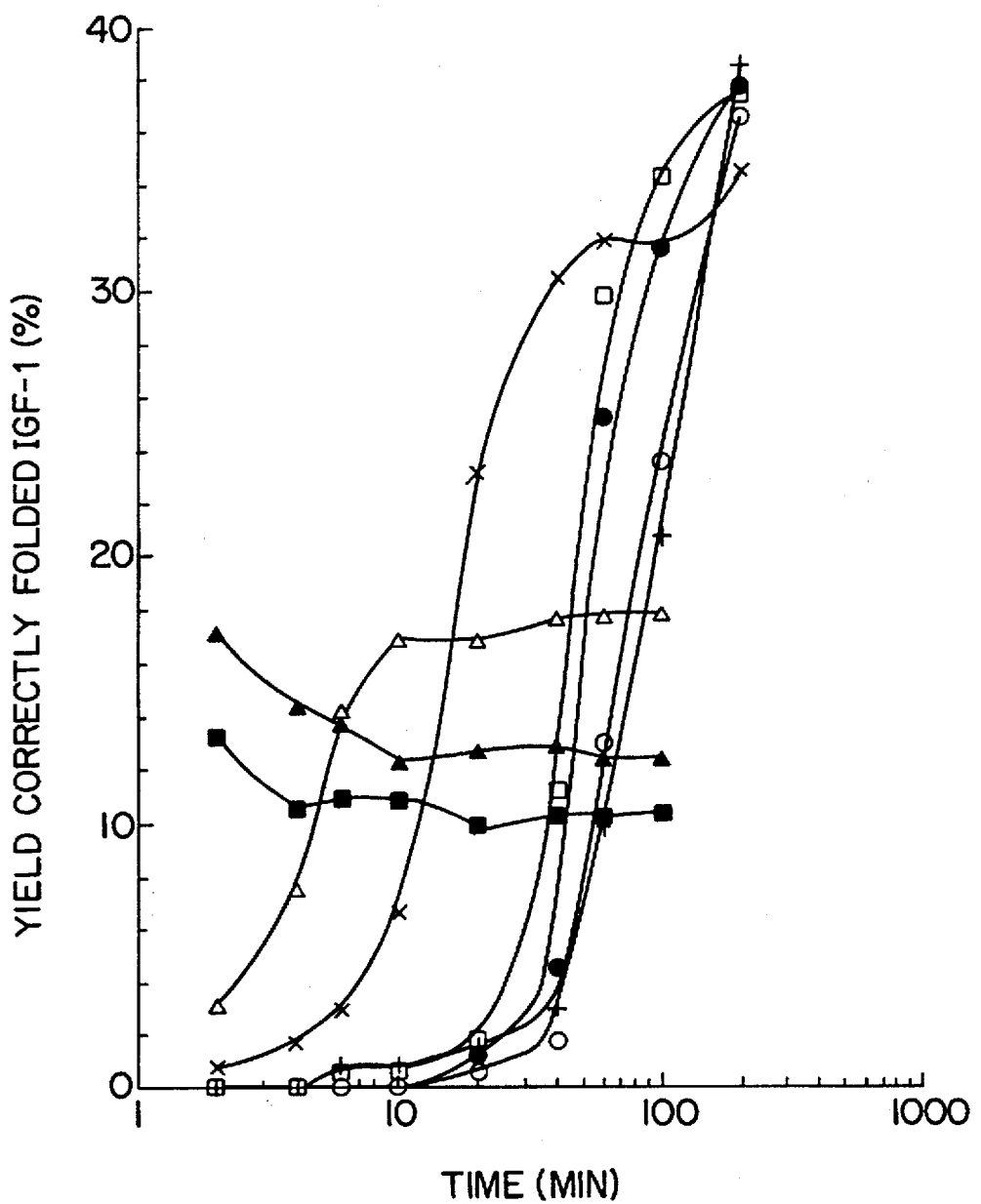
FIG. 12 shows the effect of copper concentration on the kinetics of IGF-I refolding. Refolding was conducted at 25° C. with copper chloride concentrations of trace (cross), 0.013 µM (open circle), 0.052 µM (filled circle), 0.13 µM (open square), 0.52 µM (asterisk), 1.3 µM (open triangle), 5.2 µM (filled triangle), and 13 µM (filled square).

The results shown in FIG. 12 were obtained by refolding IGF-I in solutions lacking alcoholic or polar aprotic solvent. Additional experiments showed that including alcohol in the refolding buffer did not influence the dependence of IGF-I refolding kinetics and yield on $CuCl_2$ concentration, and is not expected to influence the dependence on the concentration of other transition metals. Experiments also showed that including EDTA (1:1 molar ratio to $CuCl_2$) or o-phenanthroline (3:1 molar ratio to $CuCl_2$) in refolding solutions containing 1.3 μM $CuCl_2$ did not affect $CuCl_2$-catalyzed aerobic IGF-I oxidation kinetics.

EXAMPLE XI

Fermentation

The construction of the expression plasmid phGH4R used for expression and secretion of hGH is detailed in Chang et al., *Gene*, 55: 189–196 (1987).

*E. coli* strain 40G3 is a derivative of *E. coli* W3110. The complete genotype of 40G3 is tonAΔ phoAΔE15 Δ(argF-lac)169 deoC ΔompT degP41 (ΔPstI-kan$^r$) ilvG2096$^R$ phn (EcoB). Strain 40G3 can be derived from *E. coli* W3110 strain 16C9, which has the genotype tonAΔ phoAΔE15 Δ(argF-lac)169 deoC. The ompT deletion was introduced by P1 cotransduction with a linked Tn10 insertion in the purE gene. This strain was transduced to purine prototrophy to remove the transposon. The degP41 (ΔPstI-kan$^r$) mutation was introduced by selection for kanamycin resistance. The ilvG2096$^R$ gene was introduced by repairing an isoleucine/valine auxotroph to prototrophy using P1 transduction. Finally, the phn(EcoB) operon was introduced into the host by P1 transduction of the *E. coli* phn genes.

Competent *E. coli* 40G3 cells were transformed with phGH4R by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

A 10-L fermentor inoculum was prepared by first inoculating a two-liter shake flask containing approximately 500 mL of sterile LB medium containing 5 mg/L tetracycline with freshly thawed 0.5 mL of stock culture. This flask was incubated at 35°–39° C. for 8 hours and transferred into a 10-liter fermentor containing the production medium in the range of that described below.

| Ingredient | Quantity/Liter |
|---|---|
| glucose* | 250–350 g |
| ammonium sulfate | 3–8 g |
| ammonium hydroxide | as required to control pH 7.2 to 7.4 |
| sodium phosphate, monobasic dihydrate | 1–2 g |
| potassium phosphate, dibasic | 2–4 g |
| sodium citrate, dihydrate | 0.5–1.5 g |
| potassium chloride | 1–2.5 g |
| 25% UCON LB625 | 0.1–0.2 mL initially and as needed to control foaming |
| magnesium sulfate, heptahydrate | 1–3 g |
| tetracycline HCl | 5–20 mg |
| Hycase SF** | 5–20 g |
| NZ amine YT | 5–25 g |
| isoleucine | 0–10 g |
| methionine | 0–1 g |
| ferric chloride, heptahydrate | 10–30 mg |
| zinc sulfate, heptahydrate | 2–5 mg |
| cobalt chloride, hexahydrate | 2–5 mg |
| sodium molybdate, dihydrate | 2–5 mg |
| cupric sulfate, pentahydrate | 2–5 mg |
| boric acid | 0.5–2 mg |
| manganese sulfate, monohydrate | 1–3 mg |
| methyl phosphonate | 1.5–2.5 g |

*1–5 g/L of glucose was added to the culture initially. The remainder was fed to the culture over the course of the fermentation.
**Hycase SF was fed throughout the fermentation.

The 10-liter culture was grown at 35°–39° C. at pH 7.2–7.4 for 42–48 hours. The agitation rate was set at 650–1000 rpm and the aeration rate at 0.7–1.5 volumes of air per volume of culture per minute.

The 10-L culture was grown with continuous glucose feeding during fermentation. Production of hGH occurred after the phosphate in the medium was depleted.

Solubilization and Aqueous Extraction of Human Growth Hormone

The hGH from the above fermentation broth was solubilized by adding 240 g of urea, 20 mL of 1M glycine (pH 10), and 10 mL of 1M dithiothreitol (DTT) to 1 L of fermentation broth contained in a 2 L bottle. The pH of the resulting mixture was adjusted to pH 10 by addition of 1N NaOH. During incubation, the mixture was continuously stirred with a submerged motor driven impeller and the headspace was flushed with nitrogen. After 2 hours of incubations an aliquot was collected, centrifuged to sediment solids and the supernatant was assayed for hGH content. Reversed phase HPLC analysis showed that 31% of total hGH was in the centrifugation supernatant.

hGH was then extracted by adding 308 g of PEG-8000 and 103 g of $Na_2SO_4$ to the solubilization mixture. The resulting phase system was incubated with continued stirring and nitrogen flushing for an additional hour. Inspection of a centrifuged 14.5 mL aliquot of the phase system showed it contained 11.2 mL of clear light phase and 3.3 mL of heavy phase containing solids. Following incubation, the phase system was divided between two 1-L centrifuge bottles and centrifuged to separate the phases. Decantation of the separated phases resulted in 1.2 L of clear light phase. Reversed phase HPLC analysis showed that the light phase contained 82% of the hGH contained in the solubilization supernatant.

hGH was precipitated from the isolated light phase by adjusting to pH 4. An aliquot of the precipitate suspension was placed in a capped 15 mL tube and clarified by centrifugation. Following centrifugation, the clear supernatant was decanted into a new tube and the pellet was resuspended to 2.5 mL in 6M guanidine-HCl, 50 mM Tris-HCl (pH 9), 0.1M DTT. Reversed phase HPLC analysis showed that the resuspended pellet contained 92% of the hGH originally contained in the light phase while the supernatant contained less than 1%.

Refolding of Human Growth Hormone

Light phase containing non-native hGH was prepared using the solubilization and aqueous extraction procedure described above. Refolding buffers were prepared in 15-mL polystyrene culture tubes by addition of appropriate amounts of the following dry chemicals: urea, guanidine-HCl, NaCl, $Na_2SO_4$, and reagent grade ethanol. Each tube received 0.1 mL of a 50× buffer stock solution containing either 1M Tris-HCl (pH 8), 25 μM $CuCl_2$ or 1M glycine (pH 10), 25 μM $CuCl_2$. Other chemicals were added so as to have the indicated concentration at a final volume of 5 mL. Each tube containing refolding buffer components was brought to a final volume of 4.5 mL with purified water.

hGH refolding was initiated by diluting 0.5 mL of light phase containing reduced hGH into the previously prepared refolding buffers giving an initial hGH concentration of about 0.05 mg/mL. Tubes were capped and shaken horizontally on an orbital shaker. Each tube contained 5 mL of liquid and 10 mL of air. Refolding was allowed to occur for 12 hours after which samples were collected, diluted by a factor of 2 into an acidified buffer containing 50 mM acetic acid (pH 3), 50 mM NaCl, and analyzed by reversed-phase HPLC to determine the content of correctly folded hGH.

The object of this experiment is to show the effect of refolding buffer composition on yield of correctly folded hGH obtained during refolding. The following aspects of refolding buffer composition were investigated: salt type and concentration (0.2M $Na_2SO_4$, 0.5M NaCl), chaotrope type and concentration (0.5, 4M urea; or 0.5, 2M guanidine-HCl), solvent concentration (0, 10% [v/v] ethanol), and buffer type and pH (Tris-HCl pH 8, glycine pH 10). The yields obtained with select combinations of these components are shown in Table VIII. Inspection shows that the highest yield of correctly folded hGH was obtained by refolding under the following conditions: 20 mM glycine (pH 10), 0.5M guanidine, 0.5M NaCl, 10% (v/v) ethanol, and 0.5 μM $CuCl_2$ (sample #5).

TABLE VII

Effect of Solution Conditions on hGH Refolding Yield

| Sample # | NaCl (M) | $Na_2SO_4$ (M) | Gdn* (M) | urea (M) | EtOH % (v/v) | pH | Yield (%) |
|---|---|---|---|---|---|---|---|
| 1 | 0.5 | 0 | 0 | 0.5 | 0 | 10 | 65 |
| 2 | 0 | 0.2 | 0 | 0.5 | 10 | 8 | 61 |
| 3 | 0.5 | 0 | 0 | 4 | 10 | 8 | 71 |
| 4 | 0 | 0.2 | 0 | 4 | 0 | 10 | 65 |
| 5 | 0.5 | 0 | 0.5 | 0 | 10 | 10 | 76 |
| 6 | 0 | 0.2 | 0.5 | 0 | 0 | 8 | 4 |
| 7 | 0.5 | 0 | 2 | 0 | 0 | 8 | 69 |
| 8 | 0 | 0.2 | 2 | 0 | 10 | 10 | 71 |

*Gdn = guanidine.

The experiment described in this example was designed to allow multifactorial statistical analysis of correctly folded hGH yield data in order to assess the importance of all single factors. The results from this statistical analysis are shown in Table IX.

TABLE IX

Average Yield Correctly Folded hGH by Refolding Solution Component

A. By Salt Type and Level

| Salt | Average Yield hGH (%) |
|---|---|
| 0.5 M NaCl | 66 |
| 0.2 M $Na_2SO_4$ | 70 |

B. By Chaotrope Type

| Chaotrope Type | Average Yield hGH (%) |
|---|---|
| urea | 66 |
| guanidine (Gdn) | 71 |

C. By Chaotrope Level

| Chaotrope Level | Average Yield hGH (%) |
|---|---|
| 0.5 M urea or 0.5 M Gdn | 68 |
| 4 M urea or 2 M Gdn | 69 |

D. By Solvent Level

| [ethanol] (% v/v) | Average Yield hGH (%) |
|---|---|
| 0 | 67 |
| 10 | 70 |

E. By pH

| pH | Average Yield hGH (%) |
|---|---|
| 8 | 67 |
| 10 | 69 |

The above results show that recombinant hGH can be solubilized and excreted from cells by adding chaotrope and reductant to alkaline fermentation broth (yield of about 30% on average). Higher yields can be obtained during solubilization if cells are lysed prior to addition of solubilization agents (about a 50% yield improvement). Other small differences during solubilization include higher yield with guanidine than urea (about a 10% yield improvement) and higher yield with a moderate chaotrope concentration than with a low chaotrope concentration (about a 20% yield improvement by using 4M rather than 2M).

The aqueous extraction procedure behaved virtually identically during separation of non-native hGH from biomass as during separation of non-native IGF-I from biomass. The only difference of note involves a small preference for higher chaotrope concentration during extraction (about a 5% yield improvement by using 4M urea rather than 2M). The inclusion of higher chaotrope concentration during extraction did not significantly affect the concentration of polymer and salt needed to produce a two-phase system in which desired non-native polypeptide is enriched in light phase and biomass solids sediment in the heavy phase. Likewise, mechanical lysis of cells prior to solubilization did not affect aqueous extraction performance.

Taken together, these differences generally indicate that the larger protein hGH prefers more strongly denaturing chaotropic conditions for solubilization and is less readily excreted from the permeabilized cell than the smaller protein IGF-I.

In conclusion, the results described above for hGH clearly show that the claimed method is applicable to isolation of non-native hGH as well as IGF-I. IGF-I and hGH are substantially different proteins as they differ significantly in many of their properties. Specifically, they have different amino acid sequences, different molecular weights, different numbers and patterns of disulfide bonds, and different isoelectric points. Despite these differences, IGF-I and hGH exhibit very similar behavior during their extractive separation from biomass solids by the method of this invention.

EXAMPLE XII

Non-native IGF-I was prepared using the hosts plasmid, fermentation, and in situ solubilization procedure described in Example I, parts A–D.

Aqueous two-phase systems were produced using the following procedure: (1) solubilization mixture (whole extract) was dispensed in 1-liter roller bottles, (2) the polymers or salts indicated in Table X were added to the levels indicated in Table XI, (3) added components were dissolved by mixing with a submerged impeller for about 5 minutes, (4) the resulting mixtures were dispensed into 1-liter centrifuge bottles, and (5) the aqueous phases were separated by centrifugation at about 5,000×g for 15 minutes.

TABLE X

Material

[Ext] IGF-I whole extract
[S1] Solid sodium sulfate
[S2] Solid polyethylene glycol MW 8000
[L1] Aqueous 33.3% (w/w) dextran MW 500,000
[L2] Aqueous 50% (w/w) polyethylene glycol MW 8000
[L3] Aqueous 50% (w/w) polyvinyl pyrrolidone MW 40,000
[L4] Aqueous 20% (w/w) polyvinyl alcohol MW 50,000, 20% (w/w) ethanol

TABLE XI

Aqueous two-phase system compositions

| System | [Ext] (% w/w) (mL) | Component 1 (% w/w) (g) | Component 2 (% w/w) (g) | $V_{top}/V_{bot}$ |
|---|---|---|---|---|
| Sodium sulfate/PEG | 500 | S1 5.0 30.86 | S2 14.0 86.42 | 2.5 |
| Dextran/PEG | 500 | L1 5.0 131.6 | L2 14.0 245.6 | 3.9 |
| Dextran/ polyvinyl pyrrolidone | 500 | L1 5.0 115.4 | L3 10.0 153.9 | 1.4 |
| Polyvinyl alcohol/ ethanol/PEG | 500 | L4 5.0 266.0 | L2 14.0 297.9 | 4.9 |

The resulting light phases were (1) decanted into separate 1-liter beakers, (2) adjusted to pH 7.0 with 2N phosphoric acid to precipitate the non-native IGF-I, (3) dispensed into 250-mL centrifuge bottles, (4) centrifuged at about 5000×g for 15 min. to sediment the precipitated non-native IGF-I, and (5) decanted to separate the IGF-I pellet from the light-phase liquid.

The resulting pellets were resuspended to a final volume of 0.1 L by adding water, urea, DTT, and 50% NaOH to achieve a final condition of about 10 mg/mL IGF-I, 3M urea, 10 mM DTT, and pH 10. The resuspended pellets were then added to 0.9 L of refolding buffer contained in 2-L roller bottles. The refolding buffer had the composition: 20 mM glycine, 2M urea, 1M NaCl, 20% (v/v) ethanol, 0.5 µM copper chloride, and pH 10.5. The roller bottles were placed on their sides on an orbital shaker and gently agitated to induce surface aeration. After four hours the refolding solutions were adjusted to pH 3 by addition of 2N phosphoric acid.

The mass of IGF-I recovered after each of the described steps and the net yields are given in Table XII. The results show that non-native IGF-I can be recovered from mixtures containing biomass using several different polymer/polymer or polymer/solvent two-phase systems. Further, the yields obtained with the polymer/polymer and polymer/solvent systems are essentially equivalent to that obtained with the polymer/salt system.

TABLE XII

Yield from IGF-I Isolation Procedures

| | System | | | | | | | |
|---|---|---|---|---|---|---|---|---|
| | Sodium sulfate/PEG | | Dextran/PEG | | Dextran/ Polyvinyl Pyrrolidone | | Polyvinyl Alcohol/ Ethanol/PEG | |
| Step | IGF-I Mass (g) | Net Yield (%) | IGF-I Mass (g) | Net Yield (%) | IGF-I Mass (g) | Net Yield (%) | IGF-I Mass (g) | Net Yield (%) |
| Whole Broth | 1.7 | — | 1.7 | — | 1.7 | — | 1.7 | — |
| Whole Extract | 1.5 | 88 | 1.5 | 88 | 1.5 | 88 | 1.5 | 88 |
| Whole Extract Supernatant | 1.7 | 100 | 1.7 | 100 | 1.7 | 100 | 1.7 | 100 |
| Light Phase | 1.0 | 59 | 1.1 | 65 | 1.0 | 59 | 1.1 | 65 |
| pH7 Light Phase Pellet | 1.0 | 59 | 1.0 | 59 | 0.4 | 24 | 1.0 | 59 |
| Acidified Folded Pool | 0.5 | 29 | 0.51 | 30 | ND | ND | 0.46 | 27 |

ND = Not Determined.

What is claimed is:

1. A method for isolating from cells an exogenous polypeptide of interest, wherein the polypeptide is human growth hormone or insulin-like growth factor-I (IGF-I), in a non-native conformation and renaturing the polypeptide comprising contacting the cells with a chaotropic agent in an amount sufficient to extract the polypeptide from the cells and maintain its solubility and with an effective amount of phase-forming species, wherein the phase-forming species are a combination of polymer-salt, polymer-polymer, or polymer-solvent, to form two aqueous phases, wherein the upper phase is enriched in the polypeptide and depleted in the biomass solids and nucleic acids, and refolding the enriched polypeptide into an active conformation.

2. The method of claim 1 wherein the cells being contacted with chaotropic agent and phase-forming species are in a cell culture.

3. The method of claim 2 wherein the polypeptide of interest is in the form of inclusion bodies.

4. The method of claim 3 wherein the polypeptide is produced in prokaryotic cells.

5. The method of claim 4 wherein the polypeptide is produced in bacteria.

6. The method of claim 1 wherein the additions all take place in a fermentation vessel.

7. The method of claim 1 wherein the polypeptide is also contacted with a reducing agent in an amount sufficient to reduce at least one disulfide bond present in the polypeptide.

8. The method of claim 1 wherein, before the phase-forming species are added, the concentration of the polypeptide extracted from the cells is about 0.1 to 15 g/L.

9. The method of claim 1 wherein the concentration of chaotropic agent is about 0.1 to 9M.

10. The method of claim 1 wherein the concentration of chaotropic agent is about 0.5 to 6M.

11. The method of claim 1 wherein the chaotropic agent is added to the culture medium before the phase-forming reagents are added.

12. The method of claim 1 wherein the chaotropic agent is urea.

13. The method of claim 1 further comprising recovering the polypeptide by separating the phases.

14. The method of claim 13 further comprising isolating the polypeptide from the enriched phase by changing the pH of the phase or by adding solvent, polymer, or salt to the phase.

15. The method of claim 14 wherein the polypeptide is IGF-I and the pH of the phase is lowered.

16. The method of claim 1 wherein the salt is a sulfate, phosphate, or citrate salt.

17. The method of claim 16 wherein the salt is a sulfate.

18. The method of claim 1 wherein the polymer is polyethylene glycol, polypropylene glycol, polyvinylpyrrolidone, or a polysaccharide.

19. The method of claim 1 wherein the concentration of polymer employed is about 5% (w/w) up to the limit of solubility for the polymer and the concentration of salt employed is about 3% (w/w) up to the limit of solubility for the salt.

20. The method of claim 19 wherein the concentration of polymer employed is between about 5 and 18% (w/w) and the concentration of salt employed is between about 4 and 15% (w/w).

21. The method of claim 1 wherein from about 4 to 7% (w/w) of a phase-forming salt and from about 12 to 18% (w/w) of a phase-forming polymer is added.

22. A method for recovering from cells a biologically active exogenous polypeptide of interest, wherein the polypeptide is human growth hormone or insulin-like growth factor-I (IGF-I), comprising contacting the cells with a chaotropic agent in an amount sufficient to extract from the cells the polypeptide, which is in a non-native conformation, and maintain its solubility and with an effective amount of phase-forming species, wherein the phase-forming species are a combination of polymer-salt, polymer-polymer, or polymer-solvent, to form two aqueous phases, the upper one of which is enriched in the polypeptide and depleted in biomass solids and nucleic acids originating from the cells, recovering the polypeptide by separating the phases, and incubating said recovered polypeptide in a buffer of pH 7–12 comprising about 5–40% (v/v) of an alcoholic or polar aprotic solvent, about 0.2 to 3M of an alkaline earth, alkali metal, or ammonium salt, about 0.1 to 9M of a chaotropic agent, and about 0.01 to 15 μM of a copper manganese salt, wherein an oxygen source is introduced, so that refolding of the polypeptide occurs during the incubation.

23. A two-phase aqueous solution comprising an upper phase enriched in an exogenous polypeptide of interest, wherein the polypeptide is human growth hormone or insulin-like growth factor-I (IGF-I), in a non-native conformation and depleted in biomass solids and nucleic acids from cells in which the polypeptide was produced, wherein the aqueous solution also comprises phase-forming species, wherein the phase-forming species are a combination of polymer-salt, polymer-polymer, or polymer-solvent, and a chaotropic agent in an amount sufficient to maintain the solubility of the polypeptide, whereby the polypeptide is further characterized as refolding to an active confirmation under conditions whereby the polypeptide recovered from the upper phase is incubated in a buffer of pH 7–12 into which an oxygen source is introduced comprising about 5–40% (v/v) of an alcoholic or polar aprotic solvent, about 0.2 to 3M of an alkaline earth, alkali metal, or ammonium salt, about 0.1 to 9M of chaotropic agent, and about 0.01 to 15 μM of a copper or manganese salt.

24. The method of claim 1 wherein the IGF-I is native IGF-I.

25. The solution of claim 23 wherein the IGF-I is native IGF-I.

26. A method for isolating from cells an exogenous polypeptide of interest in a non-native conformation and renaturing the polypeptide comprising contacting, the cells with a chaotropic agent in an amount sufficient to extract the polypeptide from the cells and maintain its solubility and with an effective amount of phase-forming species consisting essentially of a combination of polymer and salt to form two aqueous phases, wherein the upper phase is enriched in the polypeptide and depleted in the biomass solids and nucleic acids, and refolding the enriched polypeptide into an active conformation.

* * * * *

UNITED STATES PATENT AND TRADEMARK OFFICE
CERTIFICATE OF CORRECTION

PATENT NO.     :     5,723,310

DATED          :     March 3, 1998

INVENTOR(S)    :     Stuart Builder et al.

It is certified that error appears in the above-identified patent and that said Letters Patent is hereby corrected as shown below:

In the claims:

Column 44, claim 22, line 13, delete [copper manganese] and insert

--copper or manganese--

Signed and Sealed this

Twelfth Day of May, 1998

*Attest:*

*Attesting Officer*

BRUCE LEHMAN

*Commissioner of Patents and Trademarks*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 485 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:1:

```
GAATTCATGA  GATTTCCTTC  AATTTTTACT  GCAGTTTTAT  TCGCAGCATC   50
CTCCGCATTA  GCTGCTCCAG  TCAACACTAC  AACAGAAGAT  GAAACGGCAC  100
AAATTCCGGC  TGAAGCTGTC  ATCGGTTACT  TAGATTTAGA  AGGGGATTTC  150
GATGTTGCTG  TTTTGCCATT  TTCCAACAGC  ACAAATAACG  GGTTATTGTT  200
TATAAATACT  ACTATTGCCA  GCATTGCTGC  TAAAGAAGAA  GGGGTATCTT  250
TGGATAAAAG  AGGTCCGGAA  ACTCTGTGCG  GCGCTGAGCT  GGTTGACGCT  300
CTGCAGTTCG  TATGTGGTGA  TCGAGGCTTC  TACTTCAACA  AACCGACTGG  350
GTACGGATCC  TCCTCTCGTC  GTGCTCCGCA  AACCGGCATC  GTTGATGAAT  400
GCTGTTTTCG  GTCCTGTGAC  CTTCGCCGTC  TGGAAATGTA  CTGCGCTCCG  450
CTGAAACCGG  CTAAGTCTGC  ATAGTCGACG  AATTC       485
```

( 2 ) INFORMATION FOR SEQ ID NO:2:

( i ) SEQUENCE CHARACTERISTICS:
        ( A ) LENGTH: 30 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:2:

```
CATGGCCGGT  CCGGAAACTC  TGTGCGGCGC  30
```

( 2 ) INFORMATION FOR SEQ ID NO:3:

( i ) SEQUENCE CHARACTERISTICS:
        ( A ) LENGTH: 22 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:3:

```
CGGCCAGGCC  TTTGAGACAC  GC  22
```

( 2 ) INFORMATION FOR SEQ ID NO:4:

( i ) SEQUENCE CHARACTERISTICS:
        ( A ) LENGTH: 51 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:4:

```
CATGGCCGGT  CCCGAAACTC  TGTGCGGTGC  TGAACTGGTT  GACGCTCTGC  50
A           51
```

( 2 ) INFORMATION FOR SEQ ID NO:5:

( i ) SEQUENCE CHARACTERISTICS:
        ( A ) LENGTH: 43 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:5:

CGGCCAGGGC TTTGAGACAC GCCACGACTT GACCAACTGC GAG 43

( 2 ) INFORMATION FOR SEQ ID NO:6:

( i ) SEQUENCE CHARACTERISTICS:
        ( A ) LENGTH: 18 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:6:

CATGGCCTCC CCATATTC 18

( 2 ) INFORMATION FOR SEQ ID NO:7:

( i ) SEQUENCE CHARACTERISTICS:
        ( A ) LENGTH: 18 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:7:

CGGAGGGGTA TAAGGAGC 18

( 2 ) INFORMATION FOR SEQ ID NO:8:

( i ) SEQUENCE CHARACTERISTICS:
        ( A ) LENGTH: 67 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:8:

TCGTCGTGCT CCCCAGACTG GTATTGTTGA CGAATGCTGC TTTCGTTCTT 50

GCGACCTGCG TCGTCTG 67

( 2 ) INFORMATION FOR SEQ ID NO:9:

( i ) SEQUENCE CHARACTERISTICS:
        ( A ) LENGTH: 70 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:9:

AGAACGCTGG ACGCAGCAGA CCTTTACATA ACGCGAGGGG ACTTTGGGCG 50

ATTTAGACGA ATCTTCGAGG 70